(12) United States Patent
Zhang et al.

(10) Patent No.: US 10,814,021 B2
(45) Date of Patent: Oct. 27, 2020

(54) PARAMAGNETIC BORON-DOPED GRAPHENE QUANTUM DOTS AND THEIR APPLICATION FOR SAFE MAGNETIC RESONANCE IMAGING

(71) Applicant: University of Washington, Seattle, WA (US)

(72) Inventors: Miqin Zhang, Seattle, WA (US); Richard Revia, Seattle, WA (US); Hui Wang, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 16/222,741

(22) Filed: Dec. 17, 2018

(65) Prior Publication Data
US 2019/0184037 A1    Jun. 20, 2019

Related U.S. Application Data

(60) Provisional application No. 62/599,515, filed on Dec. 15, 2017.

(51) Int. Cl.
| | | |
|---|---|---|
| *A61K 49/18* | (2006.01) | |
| *C01B 32/184* | (2017.01) | |
| *C01B 32/158* | (2017.01) | |
| *C01B 32/174* | (2017.01) | |

(52) U.S. Cl.
CPC ........ *A61K 49/1824* (2013.01); *C01B 32/158* (2017.08); *C01B 32/174* (2017.08); *C01B 32/184* (2017.08); *C01B 2204/02* (2013.01); *C01B 2204/04* (2013.01); *C01P 2002/54* (2013.01); *C01P 2002/82* (2013.01); *C01P 2002/84* (2013.01); *C01P 2002/85* (2013.01); *C01P 2004/04* (2013.01); *C01P 2004/51* (2013.01); *C01P 2006/42* (2013.01)

(58) Field of Classification Search
None
See application file for complete search history.

(56) References Cited

U.S. PATENT DOCUMENTS

| | | |
|---|---|---|
| 5,256,394 A | 10/1993 | Spielvogel |
| 5,286,853 A | 2/1994 | Spielvogel et al. |
| 5,877,165 A | 3/1999 | Miura et al. |
| 5,922,304 A | 7/1999 | Unger |
| 9,155,804 B2 | 10/2015 | Grimmond et al. |
| 9,642,815 B2 | 5/2017 | Singh et al. |
| 9,675,714 B1 | 6/2017 | Mohapatra et al. |
| 9,833,522 B2 | 12/2017 | Sitharaman et al. |
| 9,956,304 B2 | 5/2018 | Yang et al. |

FOREIGN PATENT DOCUMENTS

| | | | |
|---|---|---|---|
| CN | 102485647 A | 6/2012 | |
| CN | 104250006 A | 12/2014 | |
| KR | 20140130308 A | * 11/2014 | |

OTHER PUBLICATIONS

Zhang et al. Boron-doped graphene quantum dots for selective glucose sensing based on the "abnormal" aggregation-induced photoluminescence enhancement. 2014 Anal. Chem. 86: 4423-4430. (Year: 2014).*
Allemand, R-M., et al., "Organic Molecular Soft Ferromagnetism in a Fullerine $C_{60}$," Science 253:301-303, Jul. 1991.
Bogani, L., and W. Wernsdorfer, "Molecular Spintronics Using Single-Molecule Magnets," NatureMaterials 7:179-186, Mar. 2008.
Broome, D.R., "Nephrogenic Systemic Fibrosis Associated With Gadolinium Based Contrast Agents: A Summary of the Medical Literature Reporting," European Journal of Radiology 66(2):230-234, May 2008.
Cao, L., et al., "Photoluminescence Properties of Graphene Versus Other Carbon Nanomaterials," Accounts of Chemical Research 46(1):171-180, Jan. 2013.
Chang, Y.-R., et al., "Mass Production and Dynamic Imaging of Fluorescent Nanodiamonds," Nature Nanotechnology 3:284-288, May 2008.
Chen, F., et al., "$Gd^{3+}$—Ion-Doped Upconversion Nanoprobes: Relaxivity Mechanism Probing and Sensitivity Optimization," Advanced Functional Materials 23(3):298-307, 2013.
Chen, H., et al., "Gd-Encapsulated Carbonaceous Dots With Efficient Renal Clearance for Magnetic Resonance Imaging," Advanced Materials 26(39):6761-6766, Oct. 2014.
Das, S.K., et al., "Highly Porous Co(II)-Salicylate Metal-Organic Framework: Synthesis, Characterization and Magnetic Properties," Dalton Transactions 40(12):2932-2939, Mar. 2011.
Dey, S., et al., "Luminescence Properties of Boron and Nitrogen Doped Graphene Quantum Dots Prepared From Arc-Discharge-Generated Doped Graphene Samples," Chemical Physics Letters 595-596:203-208, Mar. 2014.
Eda, G., et al., "Blue Photoluminescence From Chemically Derived Graphine Oxide," Advanced Material 22(4):505-509, Jan. 2010.
Esquinazi, P., et al., "Induced Magnetic Ordering by Proton Irradiation in Graphite," Physical Review Letters 91(22):227201-1-227201-4, Nov. 2003.
Gong, N., et al., "Microwave-Assisted Polyol Synthesis of Gadolinium-Doped Green Luminescent Carbon Dots as a Bimodal Nanoprobe," Langmuir 30(36):10933-10939, Sep. 2014.
Harigaya, K., "The Mechanism of Magnetism in Stacked Nanographite: Theoretical Study," Journal of Physics: Condensed Matter 13(6):1295-1302, Feb. 2001.
Hernandez, Y., et al., "High-Yield Production of Graphene by Liquid-Phase Exfoliation of Graphite," Nature Nanotechnology 3(9):563-568, Sep. 2008.

(Continued)

*Primary Examiner* — Jennifer Lamberski
(74) *Attorney, Agent, or Firm* — Christensen O'Connor Johnson Kindness PLLC

(57) ABSTRACT

Boron-doped graphene quantum dots, methods for making the boron-doped graphene quantum dots, and methods for magnetic resonance imaging using the boron-doped graphene quantum dots.

10 Claims, 20 Drawing Sheets
(17 of 20 Drawing Sheet(s) Filed in Color)

(56) References Cited

OTHER PUBLICATIONS

Höhne, R., et al., "The Influence of Iron, Fluorine and Boron Implantation on the Magnetic Properties of Graphite," Journal of Magnetism and Magnetic Materials 320(6):966-977, Mar. 2008.

Hu, Y.H., "The First Magnetic-Nanoparticle-Free Carbon-Based Contrast Agent of Magnetic-Resonance Imaging-Fluorinated Graphene Oxide," Small 10(8):1451-1452, Apr. 2014.

Hulicova-Jurcakova, D., et al., "Combined Effect of Nitrogen- and Oxygen-Containing Functional Groups of Microporous Activated Carbon on its Electrochemical Performance in Supercapacitors," Advanced Functional Materials 19(3):438-447,2009.

Kanakia, S., et al., "Physicochemical Characterization of a Novel Graphene-Based Magnetic Resonance Imaging Contrast Agent," International Journal of Nanomedicine 8:2821-2833, 2013.

Kattel, K., et al., "A Facile Synthesis, In Vitro and In Vivo MR Studies of D-Glucuronic Acid-Coated Ultrasmall $Ln_2O_3$ (Ln = Eu, Gd, Dy, Ho, and Er) Nanoparticles as a New Potential MRI Contrast Agent," Applied Materials & Interlaces 3(9):3325-3334, Sep. 2017.

Kim, B.H., et al., "Large-Scale Synthesis of Uniform and Extremely Small-Sized Iron Oxide Nanoparticles for High-Resolution T, Magnetic Resonance Imaging Contrast Agents," Journal of the American Chemical Society 133(32):12624-12631, Aug. 2011.

Lee, E. et al., "Fabrication of Graphene Quantum Dots via Size-Selective Precipitation and Their Application in Upconversion-Based DSSCs," Chemical Communications 49(85):9995-9997, Nov. 2013.

Lee, H. et al., "Magnetic Ordering at the Edges of Graphitic Fragments: Magnetic Tail Interactions Between the Edge-Localized States," Physical Review B 72(17):174431-1-174431-8, Nov. 2005.

Li, L., et al., "Focusing on Luminescent Graphene Quantum Dots: Current Status and Future Perspectives," Nanoscale 5(10):4015-4039, May 2013.

Makarova, T.L., et al., "Magnetic Carbon," Nature 413:716-718, Oct. 2001; and Corrigendum, Nature 436:1200, Aug. 2005.

Nair, R.R., et al., "Spin-Half Paramagnetism in Graphene Induced by Point Defects," Nature Physics 8:199-202, Mar. 2012.

Narymbetov, B., et al., "Origin of Ferromagnetic Exchange Interactions in a Fullerene-Organic Compound," Nature 407:883-885, Oct. 2000.

Ohldag, H., et al., "The Role of Hydrogen in Room-Temperature Ferromagnetism at Graphite Surfaces," New Journal of Physics 12(12):123012, Dec. 2010, 10 pages.

Panich, M., et al., "On Paramagnetism in Fluorinated Graphite: EPR and Solid State NMR Study," Journal of Physics and Chemistry of Solids 62(5):959-964, Apr. 2001.

Peng, J., et al., "Superparamagnetic Reduced Graphene Oxide With Large Magnetoresistance: A Surface Modulation Strategy," Angewandte Chemie International Edition 55(9):3176-3180, Feb. 2016.

Qin, S., et al., "Strong Ferromagnetism of Reduced Graphene Oxide," Carbon 78:559-565, Nov. 2014.

Radovic, L.R., and B. Bockrath, "On the Chemical Nature of Graphene Edges: Origin of Stability and Potential for Magnetism in Carbon Materials," Journal of the American Chemical Society 12(16)7:5917-5927, Apr. 2005.

Ramakrishna Matte, H.S.S., et al., "Novel Magnetic Properties of Graphene: Presence of Both Ferromagnetic and Antiferromagnetic Features and Other Aspects," Journal of Physical Chemistry C Letters 113(23):9982-9985, Apr. 2009.

Rao, C.N.R., et al., "Unusual Magnetic Properties of Graphene and Related Materials," Chemical Science 3:45-52, 2012.

Revia, R.A., and M. Zhang, "Magnetite Nanoparticles for Cancer Diagnosis, Treatment, and Treatment Monitoring: Recent Advances," Materials Today 19(3)157-168, Apr. 2016.

Rogosnitsky, M., and S. Branch, "Gadolinium-Based Contrast Agent Toxicity: A Review of Known and Proposed Mechanisms," Biometals 29(3):365-376, Jun. 2016.

Romero-Aburto, R., et al., "Fluorinated Graphene Oxide; a New Multimodal Material for Biological Applications," Advanced Materials 25(39):5632-5637, Oct. 2013.

Sepioni, M., et al., "Limits on Intrinsic Magnetism in Graphene," Physical Review Letters 105:207205-1-207205-4, Nov. 2010.

Shen, J., et al., "Facile Preparation and Upconversion Luminescence of Graphene Quantum Dots," Chemical Communications 47(9):2580-2582, Mar. 2011.

Shin, T.-H., et al., "Recent Advances in Magnetic Nanoparticle-Based Multi-Modal Imaging," Chemical Society Reviews 44(14):4501-4516, Jul. 2015.

Soriano, D., et al., "Magnetoresistance and Magnetic Ordering Fingerprints in Hydrogenated Graphene," Physical Review Letters 107:016602, Jul. 2011.

Stephen, Z.R., et al., "Redox-Responsive Magnetic Nanoparticle for Targeted Convection-Enhanced Delivery of $O^6$-Benzylguanine to Brain Tumors," ACS NANO 8(10):10383-10395, Oct. 2014.

Stratta, P., et al., "Gadolinium-Enhanced Magnetic Resonance Imaging, Renal Failure and Nephrogenic Systemic Fibrosis /Nephrogenic Fibrosing Dermopathy," Current Medicinal Chemistry 15(12):1229-1235, 2008.

Wang, H., and S. Zhou, "Magnetic and Fluorescent Carbon-Based Nanohybrids for Multi-Modal Imaging and Magnetic Field/NIR Light Responsive Drug Carriers," Biomaterials Science 4(47):1062-1073, Jul. 2016.

Wang, H., et al., "Biocompatible PEG-Chitosan@Carbon Dots Hybrid Nanogels for Two-Photon Fluorescence Imaging, Near-Infrared Light/pH Dual-Responsive Drug Carrier, and Synergistic Therapy," Advanced Functional Materials 25(34):5537-5547, 2015.

Wang, H., et al., "Fluorescent Porous Carbon Nanocapsules for Two-Photon Imaging, NIR/pH Dual-Responsive Drug Carrier, and Photothermal Therapy," Biomaterials 53:117-126, Jun. 2015.

Wang, H., et al., "Magnetic Iron Oxide—Fluorescent Carbon Dots Integrated Nanoparticles for Dual-Modal Imaging, Near-Infrared Light-Responsive Drug Carrier and Photothermal Therapy," Biomaterials Science 2:915-923, 2014.

Wang, H., et al., "Near-Infrared- and Visible-Light-Enhanced Metal-Free Catalytic Degradation of Organic Pollutants Over Carbon-Dot-Based Carbocatalysts Synthesized from Biomass," ACS Applied Materials & Interfaces 7(50):27703-27712, Dec. 2015.

Wang, H., et al., "Paramagnetic Properties of Metal-Free Boron-Doped Graphene Quantum Dots and Their Application for Safe Magnetic Resonance Imaging," ACS Advanced Materials 29(11):1605416, Mar. 2017, 7 pages.

Wang, H., et al., "Synthesis of Boron-Doped Graphene Monolayers Using the Sole Solid Feedstock by Chemical Vapor Deposition," Small 9(8):1316-1320, Apr. 2013.

Wang, Z., et al., "Proximity-Induced Ferromagnetism in Graphene Revealed by the Anomalous Hall Effect," Physical Review Letters 114:016603-1-016603-5, Jan. 2015.

Wang, W.L., et al., "Graphene NanoFlakes With Large Spin," Nano Letters 8(1):241-245, Jan. 2008.

Wang, Y., "Room-Temperature Ferromagnetism of Graphene," Nano Letters 9(1):220-224, Jan. 2009.

Wu, X., et al., "Fabrication of Highly Fluorescent Graphene Quantum Dots Using L-Glutamic Acid for In Vitro/In Vivo Imaging and Sensing," Journal of Materials Chemistry C 1(31):4676-4684, Aug. 2013.

Xu, Y., et al., "Carbon Quantum Dot Stabilized Gadolinium Nanoprobe Prepared via a One-Pot Hydrothermal Approach for Magnetic Resonance and Fluorescence Dual-Modality Bioimaging," Analytical Chemistry 86(24):12122-12129, Dec. 2014.

Yazyev, O.V., and L. Helm, "Defect-Induced Magnetism in Graphene," Physical Review B 75(12):125408-1-125408-5, Mar. 2007.

Young, A.F., et al., "Spin and Valley Quantum Hall Ferromagnetism in Graphene," Nature Physics 8:550-556, Jul. 2012.

Zhang, A., et al., "Graphene Quantum Dots: An Emerging Material for Energy-Related Applications and Beyond," Energy & Environmental Science 5:8869-8890, 2012.

Zuo, Z., et al., "Porous B-Doped Graphene Inspired by Fried-Ice for Supercapacitors and Metal-Free Catalysts," Journal of Materials Chemistry A 1(43):13476-13483, 2013.

Choi, J.-S., et al., Self-Confirming "And" Logic Nanoparticles for Fault-Free MRI, Journal of the American Chemical Society 132:11015-11017, 2010.

(56) References Cited

OTHER PUBLICATIONS

Chong, Y., et al., "The In Vitro and in Vivo Toxicity of Graphene Quantum Dots," Biomaterials 35:5041-5048, 2014.
Eckmann, A, et al., "Probing the Nature of Defects in Graphene by Raman Spectroscopy," Nano Letters, 12:3925-3930, 2012.
Enzinger, C., et al., "Nonconventional MRI and Microstructrual Cerebral Changes in Multiple Sclerosis," Nature Reviews Neurology 11:676-686, 2015.
Fass, L., "Imaging and Cancer: A Review," Molecular Oncology 2:115-152, 2008.
Gao, Z., et al., "Small is Smarter: Nano MRI Contrast Agents — Advantages and Recent Achievements," Small 12:556-576, 2016.
Gao, J., et al., "Multifunctional Magnetic Nanoparticles: Design, Synthesis, and Biomedical Applications," Accounts of Chemical Research 42(8):1097-1107, 2009.
Kellar, K.E., et al., "NC100150 Injection, a Preparation of Optimized Iron Oxide Nanoparticles for Positive-Contrast MR Angiography," Journal of Magnetic Resonance Imaging 11:488-494, 2000.
Koikkalainen, J., et al., "Differential Diagnosis of Neurodegenerative Diseases Using Structural MRI Data," Neuroimage: Clinical 11:435-449, 2016.
Laurent, S., et al. "Magnetic Iron Oxide Nanoparticles: Synthesis, Stabilization, Vectorization, Physicochemical Characterizations, and Biological Applications," Chemical Reviews 108:2064-2110, 2008.
Lee et al.' "Paramagnetic Inorganic Nanoparticles as T1 MRI Contrast Agents," Wiley Interdiscip. Rev.: Nanomedicine and Nanobiotechnology 6:196-209, 2014.
Li, X. et al., "Carbon and Graphene Quantum Dots for Optoelectronic and Energy Devices: A Review," Advanced Functional Materials 25:4929-4947, 2015.
Matsumoto, M., et al., "Ultrahigh-Throughput Exfoliation of Graphite Into Pristine 'Single-Layer' Graphene Using Microwaves and Molecularly Engineered Ionic Liquids," Nature Chemistry 7:730-736, 2015.
NA., H.B., et al., "Development of a T1 Contrast Agent for Magnetic Resonance Imaging Using MnO Nanoparticles," Angewandte Chemie 119:5493-5497, 2007.
O'Connell, K.E., et al., "Practical Murine Hematopathology: A Comparative Review and Implications for Research," Comparative Medicine 65(2):96-113, 2015.
O'Connor, J.P.B., et al., "Imaging Biomarker Roadmap for Cancer Studies," Nature Reviews Clinical Oncology 14:169-186, 2017.
Radhakrishnan, S., et al., "Metal-Free Dual Modal Contrast Agents Based on Fluorographene Quantum Dots," Particle Systems Characterization 34:1600221, 2017, 8 pages.
Saraiva, C., et al., "Nanoparticle-Mediated Brain Drug Delivery: Overcoming Blood—Brain Barrier to Treat Neurodegenerative Diseases," Journal of Controlled Release 235:34-47, 2016.
Seo, W.S., et al., "FeCoIGraphitic-Shell Nanocrystals as Advanced Magnetic-Resonance-Imaging and Near-Infrared Agents," Nature Materials 5:971-976, 2006.
Shen, P., and Y. Xia, "Synthesis-Modification Integration: One-Step Fabrication of Boronic Acid Functionalized Carbon Dots for Fluorescent Blood Sugar Sensing," Analytical Chemistry 86:5323-5329, 2014.
Shen, Z., et al., "Iron Oxide Nanoparticle Based Contrast Agents for Magnetic Resonance Imaging," Molecular Pharmaceutics 14:1352-1364, 2017.
Thomsen, H.S., et al., "Is There a Causal Relation Between the Administration of Gadolinium Based Contrast Media and the Development of Nephrogenic Systemic Fibrosis (NSF)?" Critical Radiology 61:905-906, 2006.
Valencia, a.M., and M.J. Caldas, "Single Vacancy Defect in Graphene: Insights Into its Magnetic Properties From Theoretical Modeling," Physical Review B 96:125431, 2017, 9 pages.
Wang, 1-1., et al., "Mesoporous Carbon Nanoshells for High Hydrophobic Drug Loading, Multimodal Optical Imaging, controlled Drug Release, and Synergistic Therapy," Nanoscale 9:1434-1442, 2017.
Wang, J., et al., "Acute Toxicity and Biodistribution of Different Sized Titanium Dioxide Particles in Mice After Oral Administration," Toxicology Letters 168:176-185, 2007.
Wu, X., et al., "Fabrication of Highly Fluorescent Graphene Quantum Dots Using L-Glutamic Acid for in Vitro/in Vivo Imaging and Sensing," Journal of Materials Chemistry C 1:4676-4684, 2013.
Xiao, Y.-D., et al., "Mri Contrast Agents: Classification and Application (Review)," International Journal of Molecular Medicine 38:1319-1326, 2016.
Zhen, Z., and J. Xie, "Development of Manganese-Based Nanoparticles as Contrast Probes for Magnetic Resonance Imaging," Theranostics 2(1):45-54, 2012.
Zhou, Z., et al., "A Synergistically Enhanced T1—T2 Dual-Modal Contrast Agent," Advanced Materials 24(46):62235228, 2012. (Author Manuscript provided, PMCID: PMC3634350, available in PMC Apr. 24, 2013, 12 pages).

* cited by examiner

PARAMAGNETIC BORON-DOPED GRAPHENE QUANTUM DOTS AND THEIR APPLICATION FOR SAFE MAGNETIC RESONANCE IMAGING

CROSS-REFERENCE TO RELATED APPLICATION

This application claims the benefit of Application No. 62/599,515, filed Dec. 15, 2017, expressly incorporated herein by reference in its entirety.

STATEMENT OF GOVERNMENT LICENSE RIGHTS

This invention was made with government support under Grant No. R01 CA161953 and R01EB026890, awarded by the National Institutes of Health. The government has certain rights in the invention.

BACKGROUND OF THE INVENTION

Early detection of dysplasia by medical imaging is critical to the fight against cancer. A variety of imaging technologies have been developed and are used in the clinic, including magnetic resonance (MR) imaging, optical fluorescence imaging, X-ray computed tomography, positron-emission tomography, and ultrasound imaging. Among these imaging technologies, MR imaging is one of the most powerful noninvasive diagnostic modalities for determining the location and size of tumors. In MR imaging, arises from the differences in the MR relaxivity of hydrogen nuclei in water molecules between different tissues; these disparities are caused by the unique local magnetic field properties in which the hydrogen nuclei reside. Although the diagnosis of major diseases by MR imaging has achieved significant progress, the ability to differentiate diseased tissue from healthy tissue remains to be improved. The introduction of contrast agents to MR imaging has become increasingly important to the improvement of diagnosis by MR imaging and the contrast enhancement is achieved by increasing the rate of transverse relaxation, $r_2$, in $T_2$-weighted imaging or by accelerating the recovery of the longitudinal relaxation rate, $r_1$, in $T_1$-weighted imaging. Contrast agents used for $T_1$-weighted imaging produce hyperintense contrast, that is, images appear brighter due to the presence of the contrast agents. However, clinical $T_1$-weighted contrast agents, based primarily on Gd-based contrast agents (gadolinium chelates or complexes), have their limitations including (i) low vascular permeation, (ii) poor sensitivity limiting their diagnostic efficacy, (iii) rapid renal clearance, and (iv) the potential risk of causing nephrogenic systemic fibrosis in patients with declining renal function.

Use of nanomaterials to develop $T_1$ contrast agents may overcome the limitations of current Gd-based contrast agents. Paramagnetic metal-based nanoparticles (NPs) have been found to produce MR sensitivity higher than Gd-based complexes. However, the potential of metal leaching associated with these NPs poses safety concerns and leads to particle aggregation, therefore, hindering their use in long-term in vivo imaging applications. Although surface coating of metal-NP contrast agents may temporarily reduce the risk by suppressing the release of metal atoms into the body, the eventual degradation of the nanomaterial, which are so designed for most of nanomaterials for in vivo applications, would lead to the release of metal atoms. Additionally, the surface coating may hamper the diffusion of water molecules toward paramagnetic sites within the NPs, thus weakening observed MR signal enhancement. Furthermore, the increased hydrodynamic size (>100 nm) due to the presence of the coating often affects the ability of the NPs to cross the blood-brain barrier (BBB), thereby limiting their use in neurological MR imaging. These limitations trigger the incentive to develop small-size, metal-free MR contrast agents with minimal biological toxicity and higher imaging sensitivity.

Graphene quantum dots (GQDs) have attracted much attention in the field of biomedicine due to their biologically-benign properties both in vitro and in vivo. By doping GQDs with a non-metallic element (e.g., boron or fluorine), the otherwise non contrast enhancing GQDs become magnetic and are able to serve as contrast agents in $T_1$-weighted MR imaging. With respect to MR imaging considerations, a good $T_1$ contrast agent meets two criteria: (i) $r_1$ should be large ($r_1>5$) and (ii) the ratio of $r_2$ to $r_1$ should be small ($r_2/r_1<5$). The ability of a contrast agent to increase the $T_1$-weighted signal in an MR image is correlated to its $r_1$ value, where the greater the value of $r_1$, the greater the observed $T_1$-weighted signal. However, the contrast agent's relative effect on $r_2$ must not be significantly larger than its effect on $r_1$; if the contrast agent affects the transverse MR signal greatly, then the agent's effect on the longitudinal MR signal will be overshadowed, and any $T_1$-weighted contrast enhancement will likely be unobservable. Recently reported GQD-based contrast agents have yet to achieve the requisite low $r_2$:$r_1$ ratio and thus have been so far unable to match the contrast enhancing abilities of metal-based contrast agents. One possible limiting factor of the observed poor values for $r_2$ and $r_1$ in the existing literature is that the GQDs under study were multi-layer structures (i.e., the individual GQDs were composed of many stacked sheets of graphene held together by electrostatic forces). The structure of multi-layer GQDs inhibits the diffusion of water towards paramagnetic sites present in the lattice of the graphene layers due to substitutional dopants or vacancy defects; such occlusion of paramagnetic sites may explain the weakness of the observed $T_1$-contrast enhancement of multi-layer doped GQDs. Furthermore, although metal-free boron- or fluorine-doped GQDs are thought to be less toxic than clinical Gd-based contrast agents in biological systems based on the natures of the constituent materials, little or no parallel comparative studies in animal models have been conducted to truly evaluate the difference in toxicity between metal-free GQDs and Gd-based contrast agents.

Despite the advances in the development of MRI $T_1$ contrast agents noted above, a need exists for improved metal-free $T_1$ contrast agents. The present invention seeks to fulfill this need and provides further related advantages.

SUMMARY OF THE INVENTION

The present invention is directed boron-doped graphene quantum dots and their use for $T_1$-weighted magnetic resonance imaging.

In one aspect, the invention provides methods of obtaining a $T_1$-weighted magnetic resonance image of a tissue. In one embodiment, the method includes administering an effective dose of a contrast agent to a subject having a tissue to be imaged, wherein the contrast agent is a boron-doped graphene quantum dot; and subjecting the subject to magnetic resonance imaging to provide a $T_1$-weighted magnetic resonance image of the subject's tissue. The methods are effective in imaging heart, lung, liver, kidney, stomach, spleen, and brain tissue, as well as muscle tissue and vascular tissue.

In another aspect of the invention, boron-doped graphene quantum dots are provided. The graphene quantum dot of the invention comprises a graphene quantum dot having vacancy defects, wherein at least a portion of the vacancy defects are occupied by boron atoms, and are defined as having one or more advantageous properties selected from (i) a ratio of transverse relaxivity ($r_2$) to longitudinal relaxivity ($r_1$) from about 1 to about 5 at a magnetic field strength of from about 3 to about 14 T, (ii) a longitudinal relaxivity ($r_1$) from about 5 to about 20 $mM^{-1}$ $s^{-1}$ at a magnetic field strength of 14 T, (iii) a magnetization value from about 0.1 to about 4 emu/g at 6K and from about 0.01 to about 0.05 emu/g at 300K, or (iv) a serum half-life from about 1 to about 5 hours; one or more advantageous structural features selected from (i) the graphene of the graphene quantum dot having from one to four graphene layers, (ii) a boron atom content from about 2 to about 8% boron atoms based on total number of carbon, oxygen, and boron atoms in the graphene quantum dot as measured by X-ray photoelectron spectroscopy (XPS), or (iii) the graphene quantum dot being substantially metal free; or one or more of each of the above-noted advantageous properties and one or more of the above-noted advantageous structural features.

In one embodiment, the graphene quantum dot has a ratio of transverse relaxivity ($r_2$) to longitudinal relaxivity ($r_1$) from about 1 to about 5 at a magnetic field strength of from about 3 to about 14 T.

In another embodiment, the graphene quantum dot has a longitudinal relaxivity ($r_1$) from about 5 to about 20 $mM^{-1}$ $s^{-1}$ at a magnetic field strength of 14 T.

In a further embodiment, the graphene quantum dot has a magnetization value from about 0.1 to about 4 emu/g at 6K and from about 0.01 to about 0.05 emu/g at 300K.

In yet another embodiment, the graphene quantum dot has a serum half-life from about 1 to about 5 hours.

In one embodiment, the graphene of the graphene quantum dot has from one to four graphene layers. In one embodiment, the graphene of the graphene quantum dot is a single layer graphene.

In another embodiment, the graphene quantum dot has a boron atom content from about 2 to about 8% boron atoms based on total number of carbon, oxygen, and boron atoms in the graphene quantum dot as measured by X-ray photoelectron spectroscopy (XPS).

In a further embodiment, the graphene quantum dot is substantially metal free.

In a further aspect, the invention provides methods for making boron-doped graphene quantum dots are provided.

In one embodiment, the method for preparing boron-doped graphene quantum dots includes adding hydrogen peroxide to a solution of 4-vinylphenylboronic acid (VPBA) and a boron source in an organic solvent to provide a precursor solution; and (b) heating the precursor solution at an elevated temperature for a pre-determined time to provide boron-doped graphene quantum dots.

DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and many of the attendant advantages of this invention will become more readily appreciated as the same become better understood by reference to the following detailed description, when taken in conjunction with the accompanying drawings.

FIG. 1A is a schematic representation of the formation of the B-GQDs. FIG. 1B is a transmission electron microscope (TEM) image of representative the B-GQDs and their size distribution. FIGS. 1C-1G illustrate lattice fringe (1C), atomic force microscopy image (1D), Raman spectrum (1E), PL spectra (1F), and upconverted PL spectra (1G), respectively, of the B-GQDs.

FIG. 2A compares zero-field-cooling curves of the B-GQDs measured in an applied field of 50 Oe. FIG. 2B compares magnetization hysteresis loops of the B-GQDs at 6 K and 300 K in the range of −40 kOe<H<+40 kOe. The blue curve is the Brillouin function fitting of the 6K hysteresis curve. The inset is the enlarged magnetization hysteresis loop of B-GQDs at 300 K. FIG. 2C illustrates $T_1$-weighted MR images and $R_1$ maps of MRI phantom images of B-GQDs at different B-GQD concentrations. FIG. 2D is a plot of $1/T_1$ as a function of B-GQD concentration. The slope of the curve is defined as the specific relaxivity of $r_1$.

FIG. 3A compares in vitro cytotoxicity study of the B-GQDs performed by assessing the viability of SF763, BT474, and HEK293T cells 72 h after treatment with the B-GQDs. FIG. 3B compares distributions of the B-GQDs in various organs and tissues of nude mice receiving the B-GQDs, determined at various time points post-injection. Assessment of toxic effects of the B-GQDs on liver and kidney were by hematology analysis. FIG. 3C compares platelet (PL in figure) levels and serum alanine aminotransferase (SAA) levels. FIG. 3D compares blood urea nitrogen levels (BUN) and white blood (WBC) cells of mice receiving the B-GQDs or PBS injection, measured 24 h after administration (standard deviation of mean, n=4 mice per treatment). FIG. 3E illustrates hematoxylin and eosin (H&E) stained tissue sections of mouse heart, kidney, liver, lung and spleen, obtained from non-injected animals (bottom row, control) and those injected with the B-GQDs at a concentration of 1 mg $mL^{-1}$ (top row). The scale bar is 125 μm.

FIG. 4A illustrates in vivo $T_1$-weighted MR images of the cross-sections of mice receiving B-GQD treatment with dynamic time-resolved MRI acquired at various time points after intravenous administration. The arrows denote various organs: heart (H), liver (L), kidneys (K), spleen (Sp), and stomach (St). FIG. 4B illustrates relative $T_1$ signal intensity variation in mice injected intravenously with the B-GQDs with dynamic time-resolved MRI acquired from organs of interest before and at different time points after administration. FIG. 4C illustrates blood half-life of the B-GQD determined by fluorescence measurements. Each data point is acquired from three animals in a group.

FIGS. 13A and 13B compare magnetization hysteresis loops of the SL-BGQDs at 6 K (13A) and 300 K (13B) in the range of −10 kOe<H<+10 kOe. The insets in 13A and 13B are the enlarged magnetization hysteresis loops near 0 applied field. FIG. 13C illustrates $T_1$-weighted MR images and quantitative $R_1$ maps of SL-BGQDs at different concentrations. FIG. 13D is a plot of $1/T_1$ ($R_1$) as a function of the boron concentration in SL-BGQDs. The slope of the curve is defined as the longitudinal relaxivity, $r_1$.

FIG. 14A compares (a) $T_1$-weighted MR images of the cross-sections of mice receiving SL-BGQDs (upper panel) and Gd-DTPA (lower panel) treatments using dynamic time-resolved MR imaging acquired at various time points after intravenous administration of either contrast agent. Both grayscale and colorized images are displayed for each experimental group. The arrows point to various organs: muscle (M), spleen (S), renal cortex (RC), and renal pelvis (RP). FIGS. 14B and 14C compare relative $T_1$-weighted signal intensity in mice injected intravenously with SL-BGQDs (14B) and Gd-DTPA (14C) with dynamic time-resolved MR imaging acquired from organs of interest before and at different time points after administration of contrast agents. Statistical analysis was performed using the two-tailed Student's t-test (*$p<0.05$, $p<0.01$, *$p<0.001$).

DETAILED DESCRIPTION OF THE INVENTION

Figure 1A:
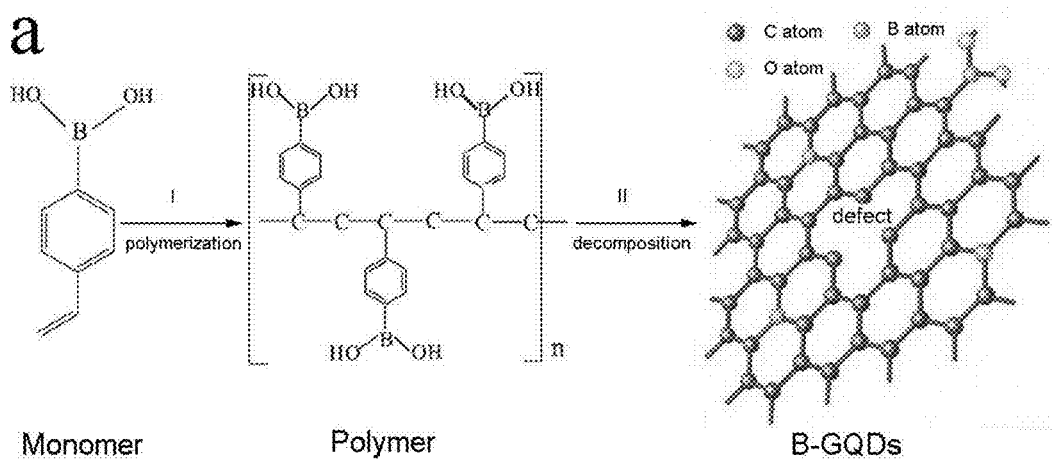
FIGS. 1A-1G illustrate the formation, structure and photoluminescent (PL) properties of representative boron-doped graphene quantum dots (B-GQDs) of the invention.

The present invention is directed boron-doped graphene quantum dots and their use for $T_1$-weighted magnetic resonance imaging.

In one aspect, the invention provides methods of obtaining a $T_1$-weighted magnetic resonance image of a tissue. In one embodiment, the method includes administering an effective dose of a contrast agent to a subject having a tissue to be imaged, wherein the contrast agent is a boron-doped graphene quantum dot; and subjecting the subject to magnetic resonance imaging to provide a $T_1$-weighted magnetic resonance image of the subject's tissue.

As used herein, the term "boron-doped graphene quantum dot" refers to a graphene quantum dot having at least a portion of the graphene's vacancy defects are occupied boron atoms.

Tissues that are advantageously imaged in the methods of the invention include heart, lung, liver, kidney, stomach, spleen, and brain tissues. Muscle tissue and vascular tissue (e.g., vasculature, such as neurovasculature) is also advantageous imaged by the methods. When the boron-doped graphene quantum dot is used for cranial magnetic resonance imaging, imaging of neurovasculature is provided demonstrating that the contrast agent is effective in crossing (e.g., permeating) the blood brain barrier.

In certain methods of the invention, the boron-doped graphene quantum dot contrast agent is administered intravenously or subcutaneously. In certain of these embodiments, the contrast agent is administered as a pharmaceutically acceptable composition. These pharmaceutically acceptable compositions include aqueous compositions that take advantage of the contrast agent's high water solubility. Representative pharmaceutically acceptable compositions include aqueous solutions for injection, such as phosphate buffered saline and dextrose solutions.

In certain embodiments, the effective amount of contrast agent administered is from about 5 to about 50 mg/kg subject.

Representative boron-doped graphene quantum dots useful in the magnetic response imaging methods of the invention have, in certain embodiments, the boron-doped graphene quantum dot has a ratio of transverse relaxivity ($r_2$) to longitudinal relaxivity ($r_1$) from about 1 to about 5 at a magnetic field strength of from about 3 to about 14 T. In certain embodiments, the boron-doped graphene quantum dot comprises graphene having from one to four graphene layers (e.g., single layer graphene or multilayer graphene). In certain embodiments, include from about 2 to about 8% boron atoms based on total number of carbon, oxygen, and boron atoms in the graphene quantum dot as measured by X-ray photoelectron spectroscopy (XPS). In certain embodiments, the boron-doped graphene quantum dot is substantially metal free.

Further details of the magnetic imaging methods and the boron-doped graphene quantum dots useful in these methods are described below.

In another aspect of the invention, boron-doped graphene quantum dots are provided.

The invention provides a graphene quantum dot, comprising a graphene quantum dot having vacancy defects, wherein at least a portion of the vacancy defects are occupied by boron atoms.

The graphene quantum dot of the invention is further defined as having one or more of the following advantageous properties, one or more of the following advantageous structural features, or one or more of each of the following advantageous properties and one or more of the advantageous structural features.

Advantageous properties of the graphene quantum dot include:

a ratio of transverse relaxivity ($r_2$) to longitudinal relaxivity ($r_1$) from about 1 to about 5 at a magnetic field strength of from about 3 to about 14 T;

a longitudinal relaxivity ($r_1$) from about 5 to about 20 $mM^{-1}$ $s^{-1}$ at a magnetic field strength of 14 T;

a magnetization value from about 0.1 to about 4 emu/g at 6K and from about 0.01 to about 0.05 emu/g at 300K; and a serum half-life from about 1 to about 5 hours.

Advantageous structural features of the graphene quantum dot include:

graphene having from one to four graphene layers;

boron atom content from about 2 to about 8% boron atoms based on total number of carbon, oxygen, and boron atoms in the graphene quantum dot as measured by X-ray photoelectron spectroscopy (XPS); and the graphene quantum dot being substantially metal free.

As used herein, the term "one to four graphene layers" refers to a graphene quantum dot in which the graphene has from one to four layers (e.g., single layer, double layer, triple layer, quadruple layer) as evidenced by the thickness of the graphene as measured by atomic force microscopy (AFM). The graphene quantum dots have thicknesses from about 0.7 (single layer) to about 3 nm (quadruple layer). In certain embodiments, the graphene quantum dot includes a multilayer graphene having up to four graphene layers. In other embodiments, the graphene quantum dot includes graphene having a single graphene layer. In certain embodiments, the graphene of the graphene quantum dot is a graphene that is a single layer graphene.

As used herein, the term "substantially metal free" refers to a boron-doped graphene quantum dot that is metal free as determined inductively coupled plasma atomic emission spectroscopy (ICP-AES) (i.e., no metal peaks detected by ICP-AES). Alternatively, the metal content of a boron-doped graphene quantum dot can be measured by X-ray photoelectron spectroscopy (XPS) (i.e., no metal peaks detected by XPS). In certain embodiments, the boron-doped graphene quantum dot has a mean diameter from about 3 to about 8 nm.

Further details of the boron-doped graphene quantum dot of the invention are described below.

In a further aspect, the invention provides methods for making boron-doped graphene quantum dots are provided.

In one embodiment, the method for preparing boron-doped graphene quantum dots includes adding hydrogen peroxide to a solution of 4-vinylphenylboronic acid (VPBA) and a boron source in an organic solvent to provide a precursor solution; and (b) heating the precursor solution at an elevated temperature for a pre-determined time to provide boron-doped graphene quantum dots.

In certain of these embodiments, the molar ratio of 4-vinylphenylboronic acid to boron source is from about 0.6 to about 2 and the molar ratio of 4-vinylphenylboronic acid to hydrogen peroxide is from about 0.001 to about 0.005.

A representative boron source is boric acid.

Organic solvents useful in the method include solvents and combinations of solvents in which hydrogen peroxide is soluble. Representative solvents include acetone and ethanol and combinations of acetone and ethanol (e.g., acetone/ethanol, 4:1 volume:volume)

Suitable elevated temperatures useful in the method range from about 200° C. to about 350° C. In one embodiment, the temperature is about 205° C.

In the method, the pre-determined time useful in the method range from about 18 to about 36 hours. In one embodiment, the pre-determined time is about 24 hours.

In certain embodiments, the method further includes dialyzing the boron-doped graphene quantum dots against aqueous media to provide an aqueous dispersion of boron-doped graphene quantum dots. The boron-doped graphene quantum dots can be collected from the aqueous dispersion.

Further details of the preparation of the boron-doped graphene quantum dot of the invention are described below.

The following describes one representative embodiment of a boron-doped graphene quantum dot, its preparation, its properties, and its usefulness in magnetic response imaging. In this representative embodiment, the boron-doped graphene quantum dot is a multilayer boron-doped graphene quantum dot. As used herein, the term "multilayer boron-doped graphene quantum dot" refers to a boron-doped graphene quantum dot in which the graphene is a single layer to multilayer graphene having up to four graphene layers. The multilayer boron-doped graphene quantum dots include single layer boron-doped graphene quantum dots and are predominately boron-doped graphene quantum dots having single layer graphene and double layer graphene as indicated by AFM.

As noted above, in one aspect, the present invention provides metal-free boron-doped graphene quantum dots (B-GODs) as a safe $T_1$ contrast agent for MRI. This magnetic property is produced by introducing both vacancies and elemental boron molecules as the substitutional defect. The B-GQDs were synthesized at 200° C. using 4-vinylphenylboronic acid (VPBA) and with boric acid as the precursor. The formation of B-GQDs (FIG. 1A) involves two steps. First, VPBA molecules form the polymer by breaking carbon-carbon double bonds under high pressure and temperature; $H_2O_2$ decomposes to form free radicals of hydroxyl (HO.) and hydroperoxyl (HOO.) and subsequently $O_2$ and $H_2O$. Second, the chemical bonds of C—H and benzene ring in the polymer and O—B in boric acid are ruptured to form boron-doped carbon-based free radicals and then larger carbon-based fragments. The hydroxyl and hydroperoxyl react with the carbon-based free radicals to form hydrophilic hydroxyl and carboxyl groups. The pressure increase caused by the produced $O_2$ and $H_2O$ further promotes the reaction to form crystallized graphene quantum dots (GQDs). Further, defects in the GQD framework provides active sites for boron doping by decomposition of VPBA and boric acid, thus leading to the formation of B-GQDs by a nuclear burst at the supersaturation point.

Figure 1B:
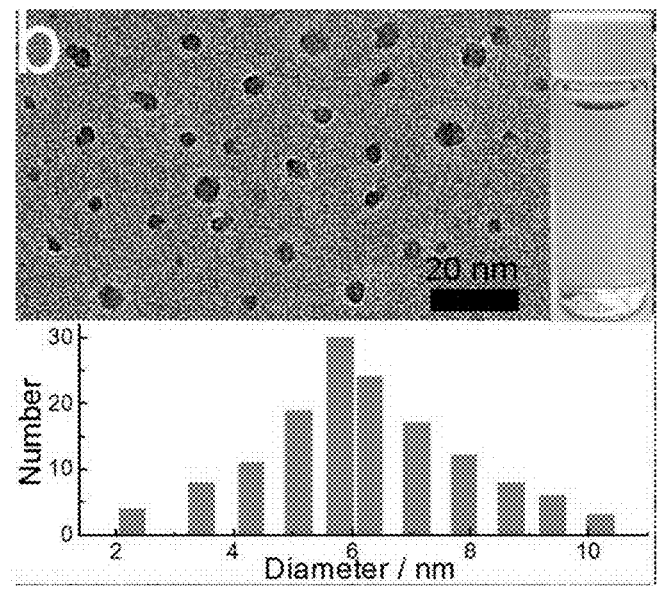
Figure 1C:
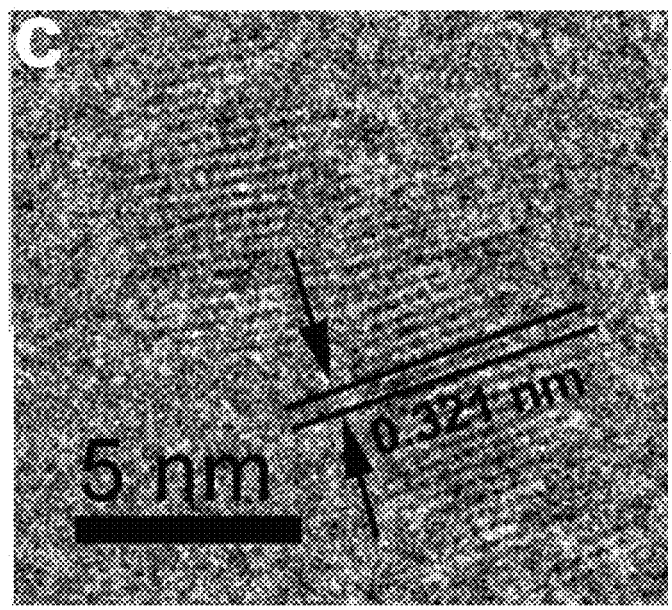
Figure 1D:
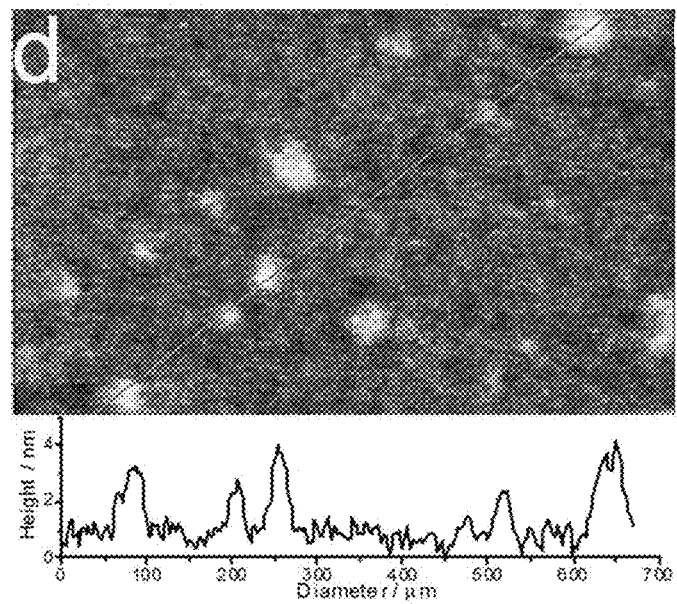
Figure 1E:
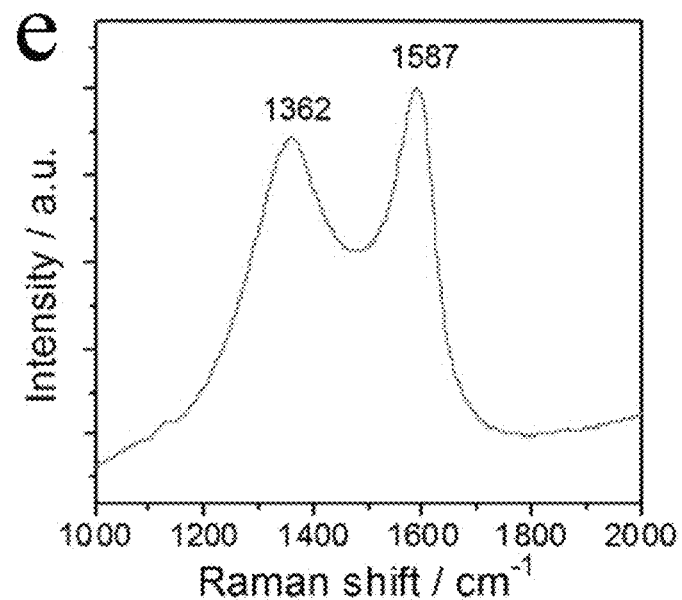

The TEM image in FIG. 1B shows that the produced B-GQDs are well dispersed and have an average size of about 5.8 nm. High-resolution TEM image (FIG. 1C) shows that B-GQDs have a crystalline structure with an interplanar distance of about 0.321 nm, corresponding well to the (002) lattice planes of graphene. The thickness of B-GQDs was characterized by atomic force microscope (AFM). As shown in FIG. 1D, B-GQDs have a height distribution peaked at about 3 nm. The crystallographic structure and phase purity of B-GQDs were examined by XRD and Raman scattering techniques, respectively. The characteristic peak of 002 in the XRD pattern can be indexed to the bulk graphite. The high-degree graphitization is also confirmed by the Raman spectrum (FIG. 1E), where the signal of the ordered G band at 1587 $cm^{-1}$ is stronger than the signal of the disordered D band at 1362 $cm^{-1}$ with a large G to D intensity ratio of 1.1. Further, the D-mode at 1362 $cm^{-1}$ in the Raman spectrum also indicates the presence of vacancy defects in B-GQDs. The XPS survey and high resolution spectra of C1s, O1s, and B1s show that carbon (69.23%), oxygen (23.64%) and boron (7.23%) are present on the surface of B-GQDs. No metal peaks were found in XPS spectra, confirming the metal-free of B-GQDs. B1 s peaks at 190.9 and 191.8 eV indicate the presence of $sp^2$ C═B bonds, confirming the successful doping of boron in GQDs.

Figure 1F:
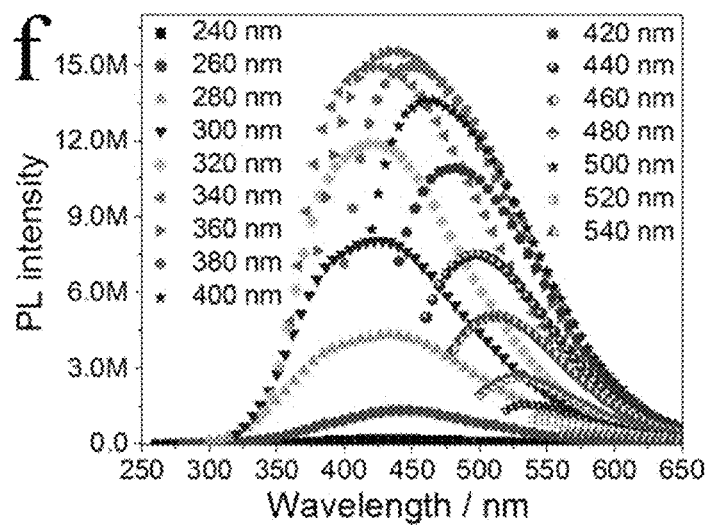
Figure 1G:
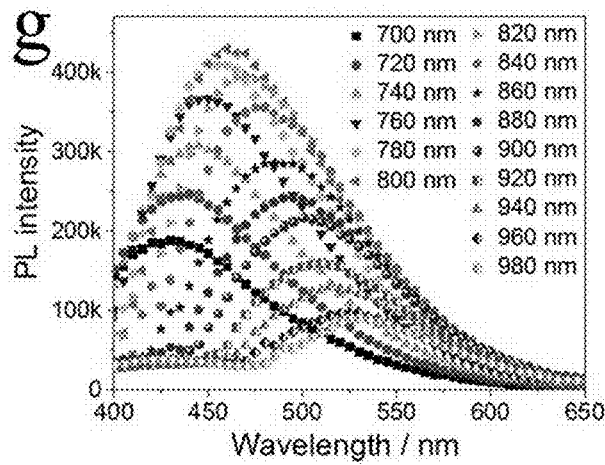

The UV-Vis absorption spectrum of B-GQDs shows an absorption band at about 244 nm resulted from $\pi$-$\pi$* transition of aromatic domains in B-GQDs. A shoulder peak at 272 nm is observed, which is attributable to n-$\pi$* transition of C═O bonds and characteristic absorption peak of GQDs. A detailed photoluminescence (PL) study of B-GQDs was carried out under different excitation wavelengths. As shown in FIGS. 1F and 1G, B-GQDs demonstrate an excitation wavelength-tunable and upconverted fluorescence property, suggesting that B-GQDs could serve as an optical imaging contrast agent with a broad range of wavelength from ultraviolet to NIR light. The photoluminescence (PL) quantum yield of B-GQDs was determined to be 11.2% using rhodamine B as a standard. This tunable PL property (emission wavelength and intensity) of B-GQDs can be attributed to the quantum confinement of conjugated $\pi$-electrons in an $sp^2$ network, the presence of defects (including heteroatom doping), multiphoton active processes and potential anti-stokes transition. The hydrophilic carboxyl groups including O—H stretching at 3428 $cm^{-1}$ and C═O stretching mode at 1701 $cm^{-1}$ on the surface of B-GQDs endow them good water-solubility (FIG. 1B, inset).

Figure 2A:
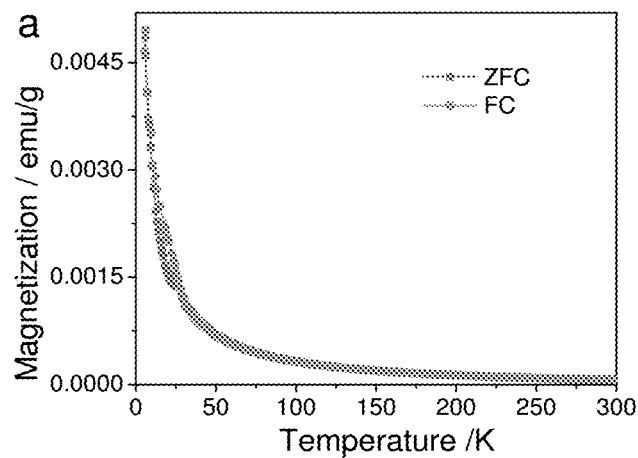
FIGS. 2A-2D illustrate magnetic properties and in vitro MRI of representative B-GQDs of the invention.
Figure 2B:
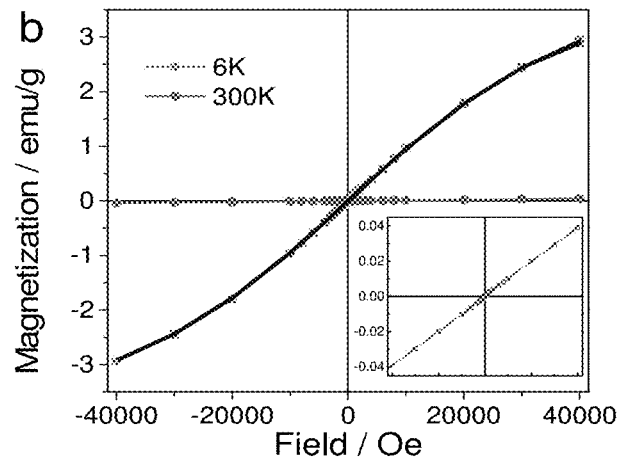

Magnetism of B-GQDs was assessed with a superconducting quantum interference device magnetometer (SQUID). Great care was taken during the preparation of B-GQDs to ensure that there were no metal impurities. The samples for SQUID were first assessed by inductively coupled plasma atomic emission spectroscopy (ICP-AES). Results show that no Gd, Fe, Co and Mn elements are present in B-GQDs that may otherwise also contribute to the paramagnetism. FIG. 2A shows the field sensitive temperature dependence of magnetization measured at fields of 50 Oe in both the zero field cooled (ZFC) and field cooled (FC) states. The magnetic moments monotonically increase with decreasing temperature down to 5 K. The steep increase in magnetization at low temperatures indicates the strong paramagnetic behavior of B-GQDs. The comparison of the magnetic hysteresis (M-H) curves at 6K and 300K in FIG. 2B confirms the strong paramagnetic behavior of B-GQDs, which have a magnetization value of 2.935 emu/g and 0.0398 emu/g, respectively, at these two temperatures.

The magnetization value of B-GQDs is lower than those of paramagnetic lanthanide oxide NPs (e.g., $Gd_2O_3$, 6.25 emu/g; $Eu_2O_3$, 1.38 emu/g) at 300 K, but, as noted above, metal-containing materials pose a safety concern for medical applications. On the other hand, most metal-free graphene-based materials with defects demonstrate a ferromagnetic property at 300 K. However, materials with ferromagnetic properties cannot serve as positive $T_1$ CAs. Metal-free graphite and metal-free graphene oxide could also produce paramagnetism by introducing dipolar C—F bonds. For example, it has been reported that graphite doped with fluorine demonstrates a paramagnetic property (0.82 emu/g). However, application of these materials in medicine is limited by potential toxicity, poor stability, high uptake by liver, and low tissue penetration depth primarily due to their larger sizes (1 μm).

Figure 5:
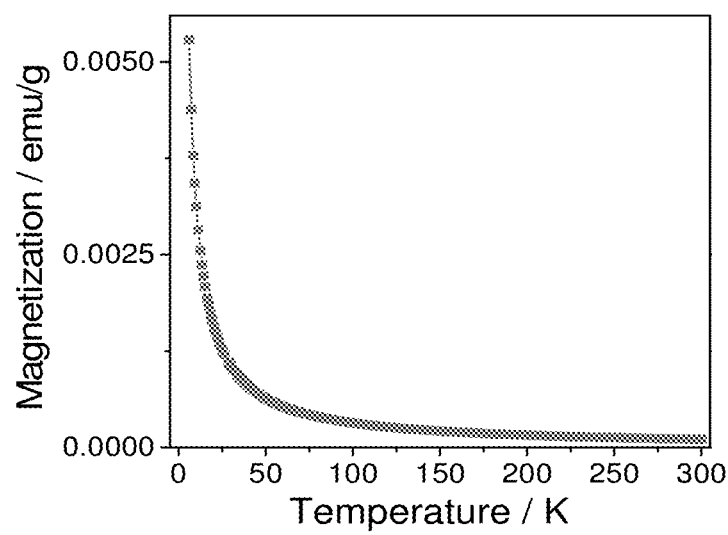
FIG. 5 compares zero-field-cooling (ZFC) and field-cooling (FC) curves of representative paramagnetic B-GQDs of the invention measured in an applied field of 50 Oe.
Figure 6:
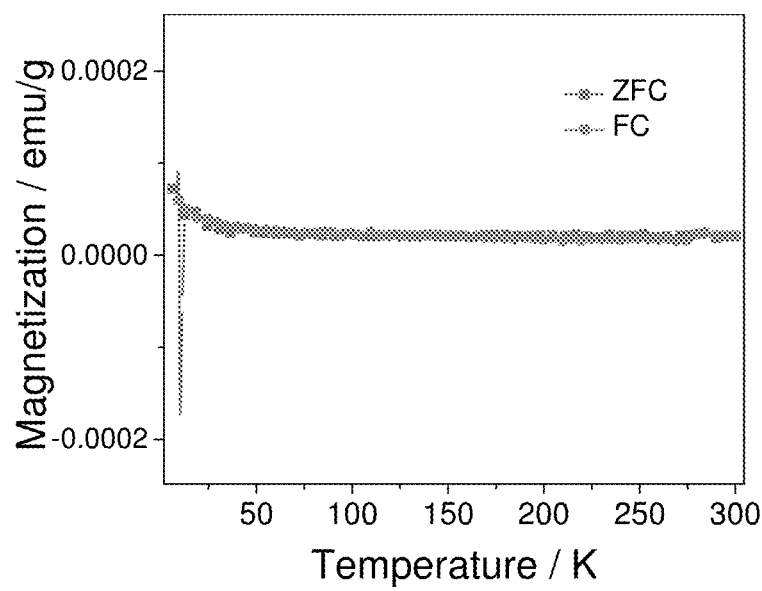
FIG. 6 illustrates zero-field-cooling and field-cooling curves of the GQDs measured in an applied field of 50 Oe.

FIG. 5 shows the Curie-Weiss law fitting (M=c*H/T) of the paramagnetic component of B-GQDs with a Curie constant of $6.25 \times 10^{-4}$. To investigate the influence of boron doping on the magnetism of GQDs, pure GQDs were prepared as a control using a synthesis method similar to the method for synthesizing B-GQDs. Compared to B-CQDs (FIG. 2A), GQDs display weak diamagnetism (FIG. 6), which indicates that the boron doping can induce the transition of GQDs from weak diamagnetism to paramagnetism. The paramagnetism of B-GQDs may be attributed to the local magnetic moments of dangling bonds. Such a bond may produce a localized spin and further convert a graphite $sp^2$ bond into an $sp^a$ bond at the expense of a it bond. Localized spins in a high boron concentration region behave like isolated spins, therefore, leading to the formation of paramagnetic centers.

Figure 2C:
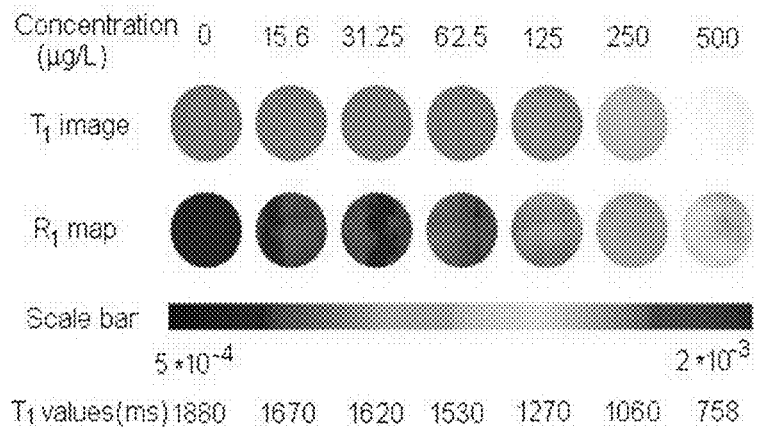
Figure 2D:
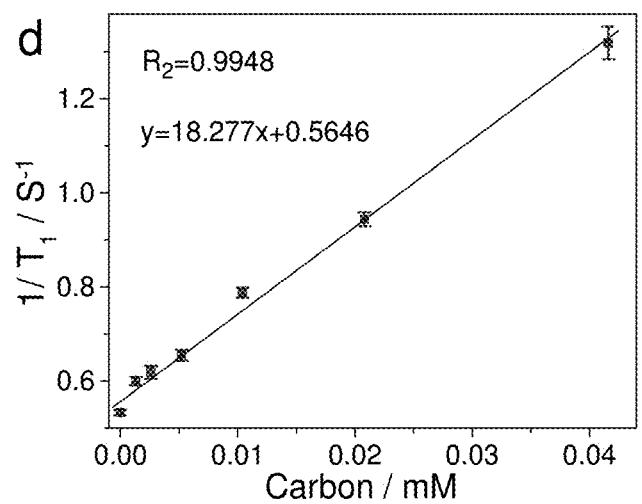

Given their paramagnetic behavior, B-GQDs were investigated as a $T_1$ CA for MRI both in vitro and in vivo. As shown in FIG. 2C, the $T_1$ signal intensity increases with increasing B-GQD concentration (corresponding to an increase in carbon concentration). This indicates the capability of our MF B-GQDs to enhance contrast in $T_1$-weighted MRI. $T_1$ values were then plotted as $1/T_1$ as a function of carbon molar concentration (FIG. 2D). The relaxation $(1/T_1)$ exhibits a linear relationship with carbon molar concentration, and the longitudinal relaxivity, $r_1$ (the slope of the best fit line in this linear relation) of B-GQDs is 18.277 $mM^{-1}$ $s^{-1}$. Comparatively, the $r_1$ of GQDs is only 0.0038 $mM^{-1}$ $s^{-1}$, indicating that the boron doping of GQDs substantially increase the longitudinal relaxivity. Also notably, although the magnetization value of B-GQDs is lower than paramagnetic lanthanide oxide NPs as mentioned above, the $r_1$ relaxivity of B-GQDs is much greater than these metal-based T1 CAs ($Gd_2O_3$, 4.25 $mM^{-1}$ $s^{-1}$; $Eu_2O_3$, 0.006 $mM^{-1}$ $s^{-1}$). In addition, the $r_1$ relaxivity of B-GQDs is also much greater than the relaxivity of the most commonly-used clinical $T_1$ CA (i.e., Gd-DTPA, $r_1$=5.39 $mM^{-1}$ $s^{-1}$). Further, although it is reported that the introducing Gd into carbon dots could increase the relaxivity of carbon dots, the $r_1$ relaxivity of B-GQDs is still greater than that of reported Gd-carbon dots ($r_1$=11.35 mM$^{-1}$ s$^{-1}$). This suggests that the boron doping is more efficient than metal doping in carbon-based materials in enhancing the relaxivity. This may be due to the smaller diameter of doped boron atoms that produce more paramagnetic centers in nanostructured carbon materials. The B-GQDs are the first metal-free contrast agent that provides contrast enhancement in $T_1$-weighted imaging.

Figure 3A:
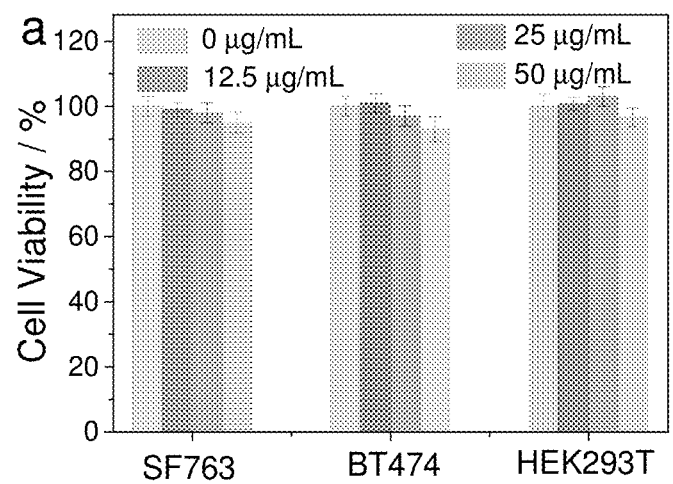
FIGS. 3A-3E illustrate in vitro and in vivo biocompatibility assessment of representative B-GQDs of the invention.

The cytotoxicity of B-GQDs were evaluated with two tumor cell lines (SF763 and BT474) and one healthy cell line (HEK293T). More than 96% of cells from all three cell lines survived 72 h after treatment with B-GQDs at different concentrations. This indicates that B-GQDs are nontoxic to the tested cells (FIG. 3A).

Figure 3B:
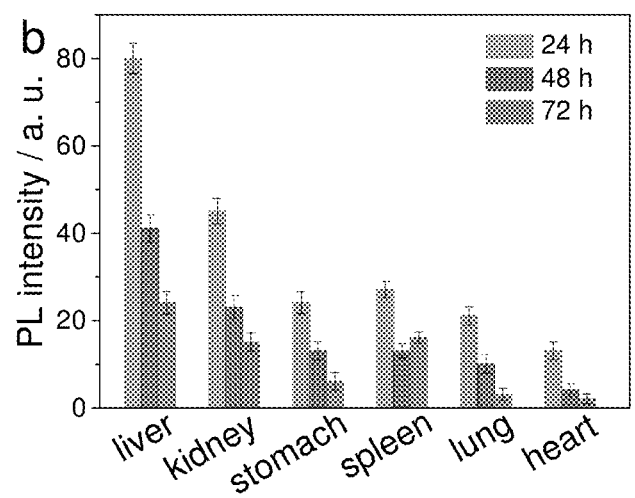
Figure 3C:
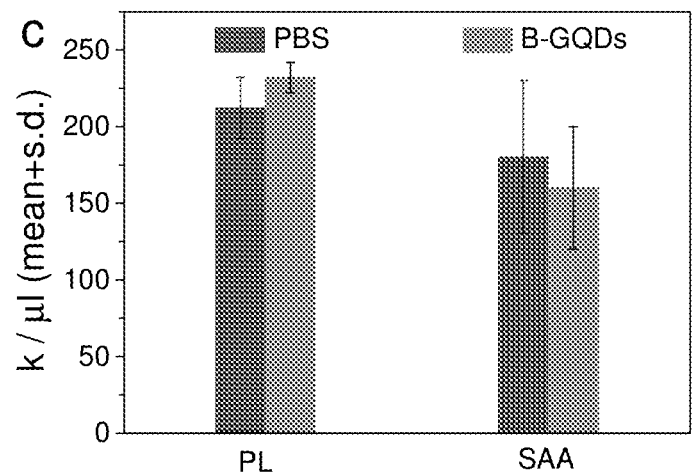
Figure 3D:
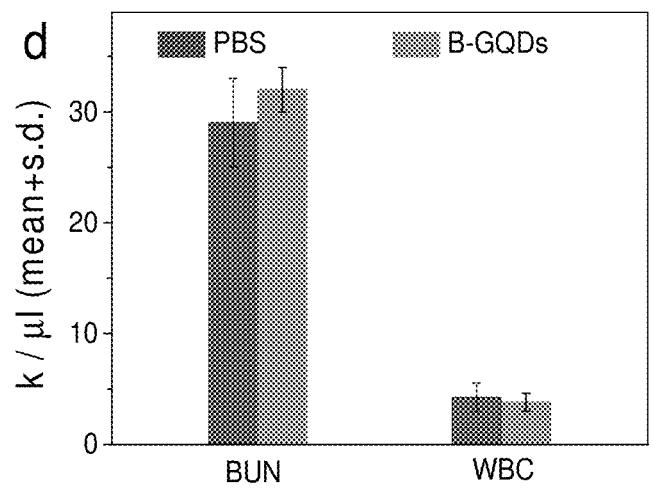
Figure 3E:
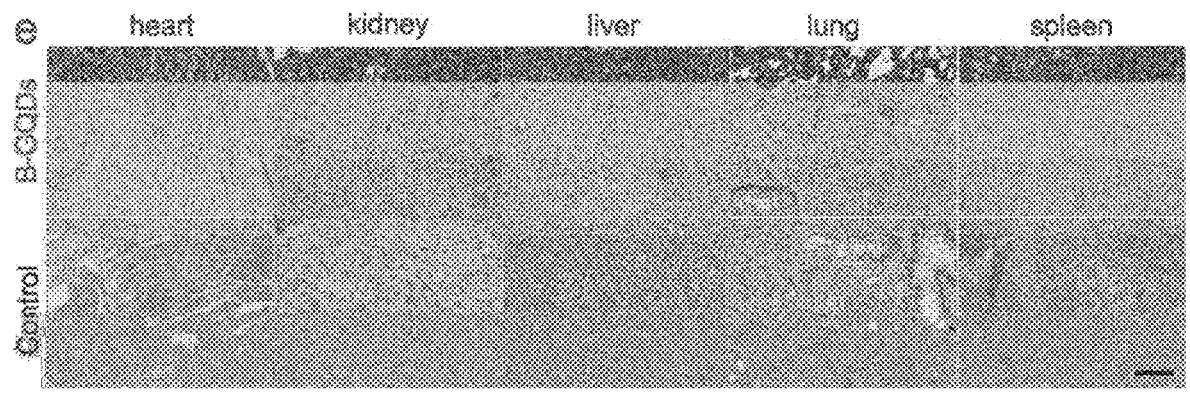

The biodistribution of B-GQDs was evaluated by injecting B-GQDs into wild-type of mice and quantifying the fluorescence intensities of B-GQDs in organs of interest (FIG. 3B). Results showed significant portions of B-GQDs were taken up by liver, stomach and spleen while lesser amounts were found in lung and heart at 72 h post injection. B-GQDs showed no obvious systemic toxicity as demonstrated by assays of serum markers of liver and kidney functions (FIGS. 3C and 3D). As shown in FIGS. 3C and 3D, the levels of serum alanine aminotransferase, white blood cells, platelet, and blood urea nitrogen were similar between PBS and B-GQD treated animals, suggesting that B-GQDs do not induce liver toxicity at the given dosage despite the large accumulation of B-GQDs in liver. The biocompatibility of B-GQDs in vivo was assessed by histological analysis of various tissues from mice treated by intravascular injection with B-GQDs or PBS solution (as control). The analysis of tissue sections showed that the tissues from the mice receiving B-GQDs appear similar to those from control animals (receiving PBS), and no evidence of toxicity was observed (FIG. 3E).

Figure 4A:
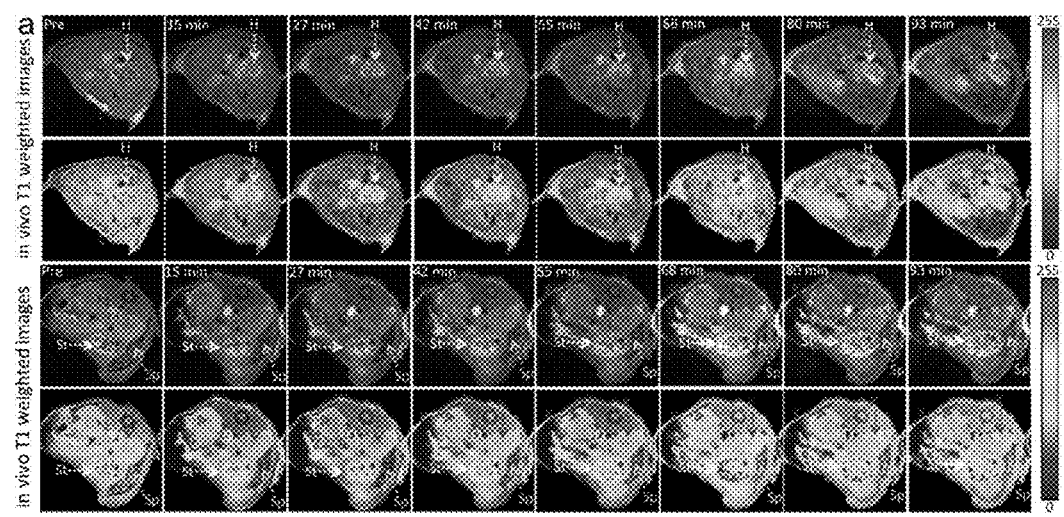
FIGS. 4A-4C illustrate in vivo MRI of mice receiving representative B-GQDs of the invention.
Figure 4B:
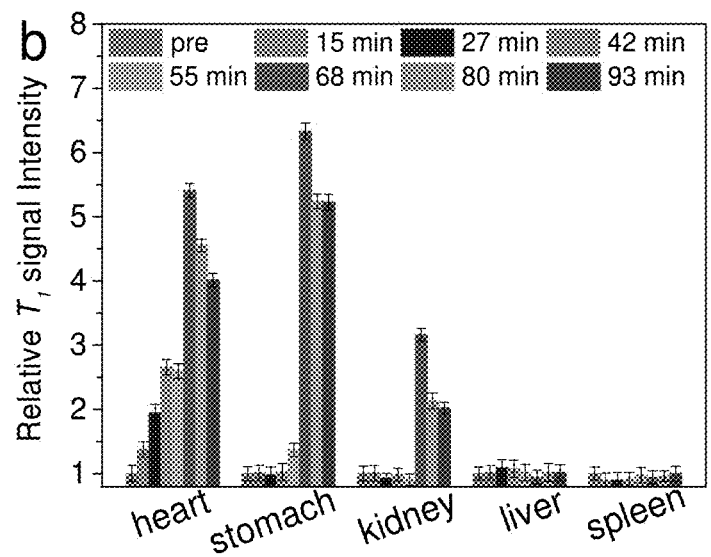
Figure 4C:
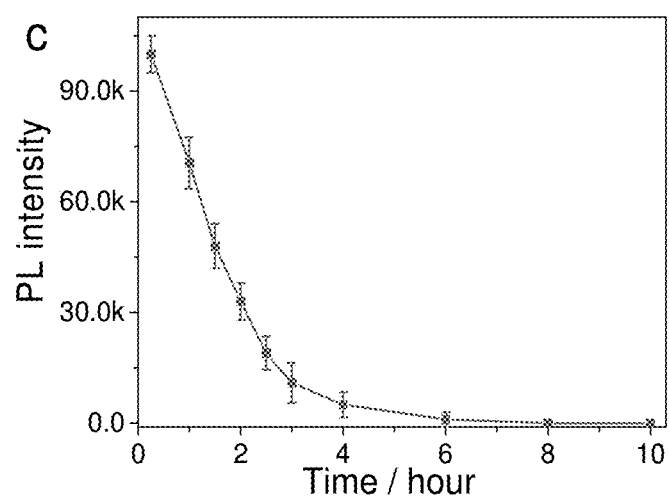

To evaluate the MRI imaging capability of B-GQDs in mice, B-GODs were administered with B-GQDs through subcutaneous injection. The B-GQDs demonstrated a substantial contrast enhancement as compared to PBS-injected solution. The contrast enhancement by B-GQDs was further assessed by intravenous injection of 100 μL dispersive PBS solution containing B-GQDs (0.2 mg) into wide-type mice. $T_1$-weighted MR images of the cross-section views of mice centered on heart, liver, kidney, stomach, and spleen (FIG. 4A) were acquired before and after the injection. The signal intensity of positive contrast increased over time throughout the duration of the experiment (68 min) in all organs, followed by a weak decay at the end of the experiment (about 90 min). In these $T_1$-weighted images, heart and stomach show higher positive contrast enhancement than kidney, spleen, and liver. Quantitatively, the $T_1$ signal intensity (FIG. 4B) was increased by 403.4% and 522.4% for heart and stomach, respectively, at 93 min post-injection, relative to the signal intensities of these of these organs before the injection. The enhanced signal sustains for more than 1.5 h (consistent with the blood half-life of B-GQDs in FIG. 4C), which is seven times longer than a commonly-used Gd-based clinical MRI T1 CA (<10 min).

Figures 7A, 7B, 7C:
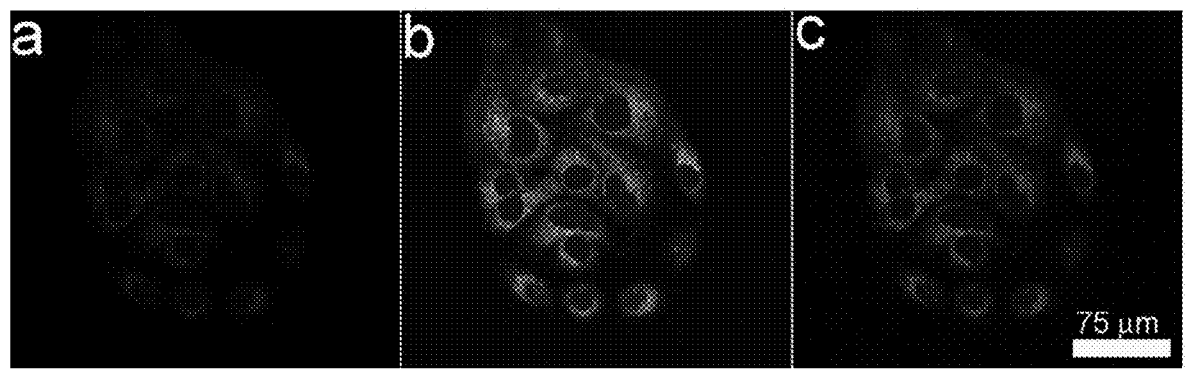
FIGS. 7A-7C are laser scanning confocal microscopic images of SF763 cells incubated with representative B-GQDs of the invention, acquired under various excitation wavelengths: 405 nm (7A), 488 nm (7B), and 546 nm (7C).
Figures 8A, 8B, 8C:
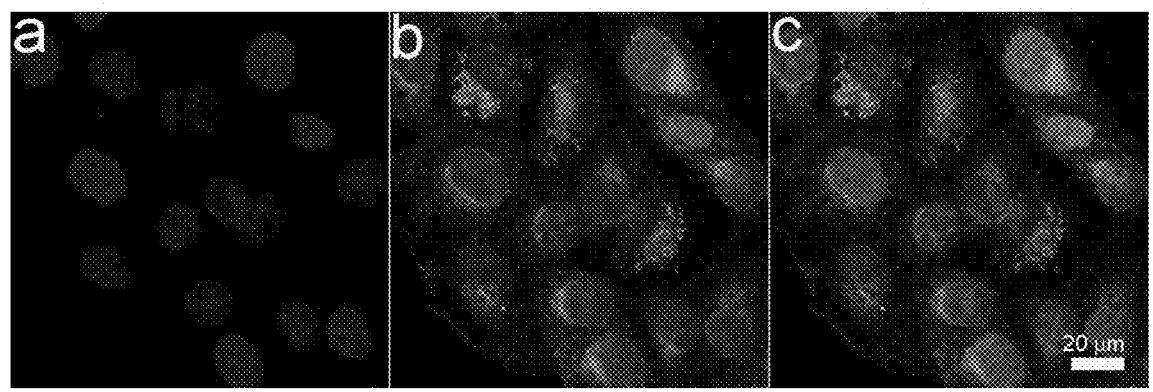
FIGS. 8A-8C illustrates two-photon fluorescence cellular imaging: DAPI nuclear stain (8A), two-photon fluorescence (8B), and overlaid images of SF-763 cells incubated with representative B-GQDs (8C). Excitation laser wavelength is 900 nm.
Figures 9A, 9B, 9C, 9D:
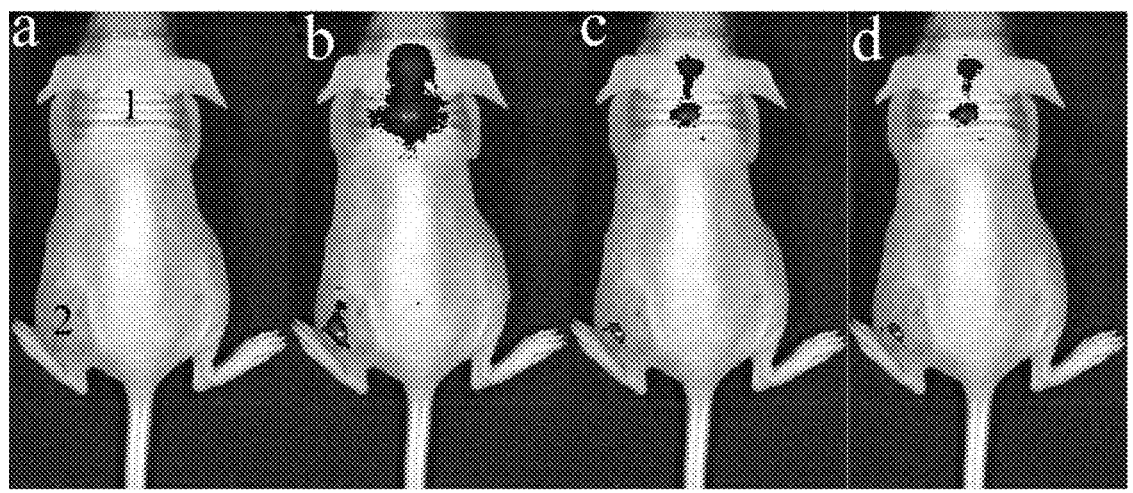
FIGS. 9A-9D are in vivo NIR fluorescence images of mice treated with representative B-GQDs of the invention through subcutaneous injection, acquired under various excitation wavelengths: white light (9A), 670 nm (9B), 710 nm (9C), and 745 nm (9D). Numbers 1 and 2 indicate the locations of the subcutaneously-injected B-GQDs. Red fluorescence of B-GQDs, indicates that B-GQDs can be used as an in vivo imaging contrast agent without using an expensive and unstable organic dye.
Figures 10A, 10B, 10C, 10D:
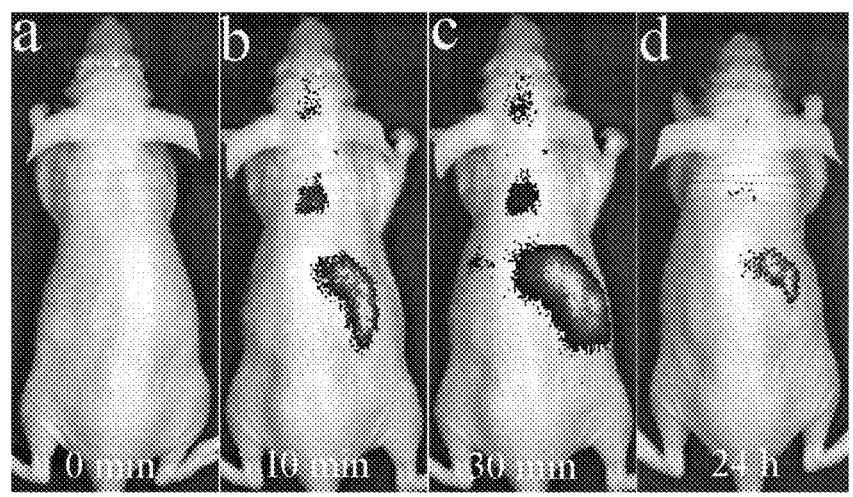
FIGS. 10A-10D are in vivo NIR fluorescence images of mice treated with representative B-GQDs of the invention through intravenous injection acquired with the excitation wavelength of 710 nm at four time points before and after injection: 0 min (10A), 10 min (10B), 30 min (10C), and 24 h (10D).
Figure 11:
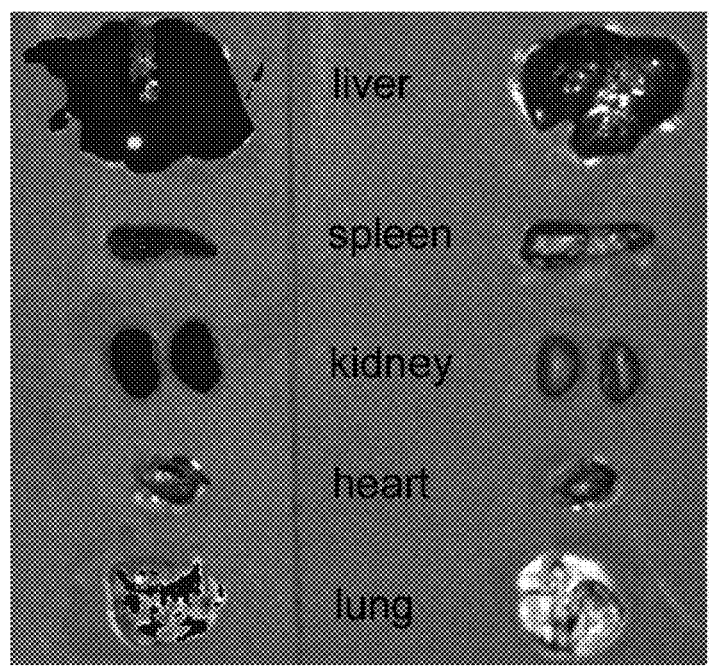
FIG. 11 compares NIR images of heart, kidney, liver, lung and spleen from B-GQDs (left) and PBS (right) treated mice at 72 h post-injection, acquired using an excitation wavelength of 710 nm.

In addition to serving as a positive $T_1$ CA for MRI, B-GQDs demonstrate fluorescent property that makes them a marker in optical imaging. FIGS. 7A-7C shows the laser scanning confocal images of SF-763 cells incubated with B-GQDs, acquired under laser irradiation at wavelengths of 405, 488, and 546 nm, respectively. As shown, B-GQDs produced a bright fluorescence and can illuminate SF-763 cells in multicolor forms. FIGS. 8A-8C shows images of fluorescence, DAPI nuclear stained SF-763 cells after uptaking B-GQDs and excited by a wavelength of 900 nm using two-photon microscopy. This demonstrates that cells can also be illuminated by the upconverted fluorescence emitted by B-GQDs under excitation of NIR laser irradiation. To further investigate applicability of B-GQDs for in vivo NIR imaging, nude mice were injected subcutaneously and intravenously with B-CQDs, respectively. As shown in FIGS. 9A-9D, fluorescence of B-GQDs can be observed in mice treated with subcutaneous injection of B-GQDs at excitation wavelengths of 670, 710, and 745 nm at both subcutaneous injection sites. The mice treated by intravenous injection of B-GQDs remained emitting NIR fluorescence from liver 24 h post-injection at an excitation wavelength of 710 nm (FIGS. 10A-10D). Furthermore, NIR signals were observed at an excitation wavelength of 710 nm from various organs of the mice treated with intravenously injected B-CQDs 72 h post-injection (FIG. 11). The PL spectrum of B-GQDs under an excitation wavelength of 710 nm confirmed their NIR emission with a maximum peak at 806 nm. This result validates their potential use as optical nanoprobes in biomedical imaging.

The following describes a second representative embodiment of a boron-doped graphene quantum dot, its preparation, its properties, and its usefulness in magnetic response imaging. In this representative embodiment, the boron-doped graphene quantum dot is a single layer boron-doped graphene quantum dot. As used herein, the term "single layer boron-doped graphene quantum dot" refers to a boron-doped graphene quantum dot in which the graphene is a single layer graphene. These boron-doped graphene quantum dots are predominately boron-doped graphene quantum dot having a single graphene layer.

Described herein are single-layer boron-doped graphene quantum dots (SL-BGQDs) that demonstrate excellent water-solubility and a small size distribution (4.6±1.4 nm). SL-BGQDs have a longitudinal relaxivity ($r_1$=8.5 mM$^{-1}$ s$^{-1}$) higher than and a $r_2/r_1$ ratio (1.08) similar to the clinical $T_1$ contrast agent gadolinium diethylene penta-acetic acid (Gd-DTPA, $r_1$=4.3 mM$^{-1}$s$^{-1}$, $r_2/r_1$=1.16) at a magnetic field strength of 14 T. Importantly, SL-BGQDs do not exhibit any cytotoxicity in 4T1, SF763, or B16F10 cells. $T_1$-weighted MR imaging of the abdomens and craniums of mice receiving either SL-BGQDs or Gd-DTPA via tail-vein injection were compared. Mice injected with SL-BGQDs exhibited better contrast enhancement in most organs including the kidneys, liver, spleen, and the vasculature compared to mice injected with Gd-DTPA. Furthermore, a mouse model was used to conduct a parallel comparison of the toxicity profiles between SL-BGQDs and Gd-DTPA by monitoring for any stress-induced response resulting from the endoplasmic reticulum (ER), inflammation, and hematological or histopathological abnormalities. Confocal microscopy images of histological neural tissues demonstrate the ability of SL-BGQDs to bypass the BBB. These results indicate that SL-BGQDs are a promising metal-free, carbon-based nanomaterial platform capable of providing clinically relevant MR contrast enhancement while maintaining a biologically innocuous response profile.

Figure 12A:
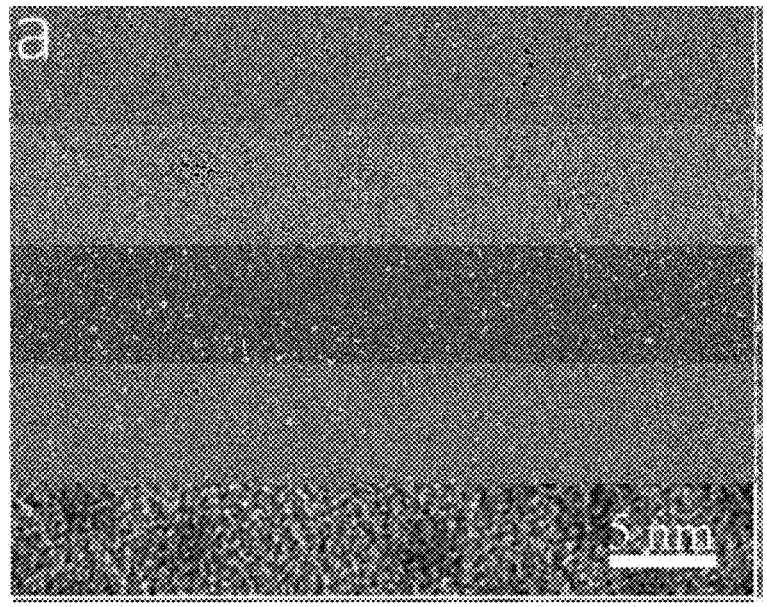
FIGS. 12A-12F illustrate physicochemical properties of representative SL-BGQDs of the invention: TEM (12A) and HRTEM (12B) images of SL-BGQDs (red circles in 1B mark the locations of vacancy defects in SL-BGQDs); AFM image (12C) and the height profile (12D) corresponding to the white line segment shown in (12C); XPS (12E) and UV absorption (12F) spectra of SL-BGQDs. The inset in 1F shows photographs of the aqueous dispersion of SL-BGQDs with (right bottle) and without (left bottle) UV light radiation (365 nm).
Figure 12B:
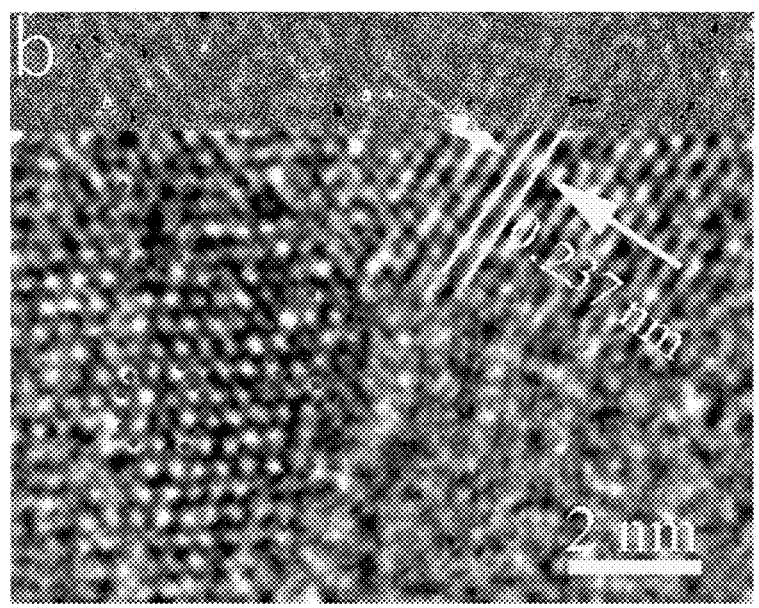
Figure 12C:
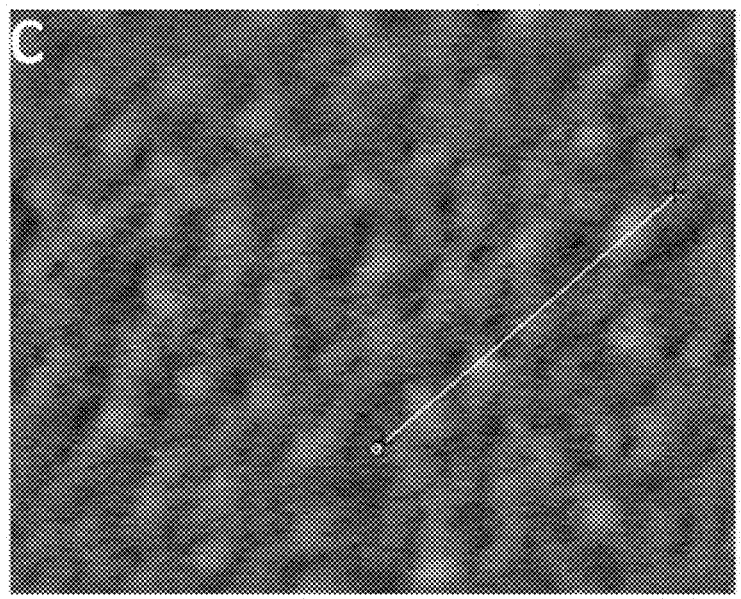
Figure 12D:
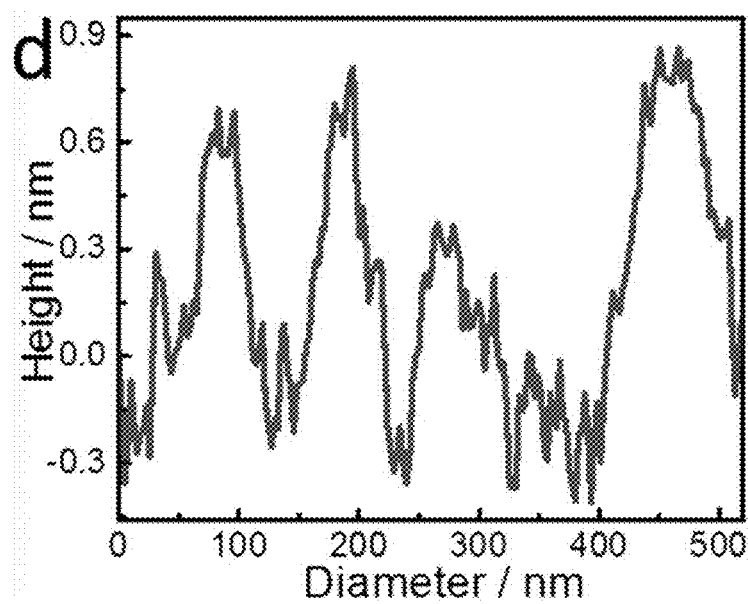

Liquid-gas interfacial growth has been proved as an effective strategy for preparing two dimensional nanostructures. As described above, multi-layer B-GQDs (having about 4-5 graphene layers) were synthesized via a simple one-step solvothermal process using 4-vinylphenylboronic acid (VPBA) and boric acid as precursors and organic solvent (e.g., acetone/ethanol)/hydrogen peroxide solution. In order to synthesize SL-BGQDs described herein, the same precursors and experimental condition as described above and herein for multilayered B-GQDs were used except that an increased amount (about 2×) of hydrogen peroxide was used to create increased liquid-gas interface to decompose VPBA molecules, and thus form GQDs with a smaller size or narrower size distribution as well as fewer layers than the multilayered B-GQDs (for example, as described herein). The TEM image shown in FIG. 12A shows that SL-BGQDs are well dispersed and have an average size of 4.6±1.4 nm. The high-resolution TEM (HRTEM) image in FIG. 12B further reveals that SL-BGQDs have a superlattice structure with an interplanar distance of about 0.237 nm, corresponding to the (100) lattice planes of graphite. In addition, vacancy defects in SL-BGQDs are identified in the image (red circles). The thickness of the SL-BGQDs was characterized by atomic force microscopy (AFM). SL-BGQDs have a height distribution peaked at about 0.7 nm (FIGS. 12C and 12D), indicating a single-layer structure of SL-BGQDs. The single-layer structure eliminates the possibility of spin pairing of boron in adjacent graphene layers and facilitates bidirectional attachment of water molecules on the boron atoms in GQDs, which results in increase in magnetic properties and MR imaging contrast enhancement.

Powder X-ray diffraction (XRD) patterns and Raman spectroscopy were used to obtain further crystallographic structure and phase purity information, respectively, of SL-BGQDs. The characteristic peak at about 20° in the XRD pattern can be indexed to the bulk graphite. Many characteristics exhibited by high-defect-density graphene are confirmed by the Raman spectrum. A high degree of graphitization is observed within SL-BGQDs as evidenced by the large Raman peak at 1574 cm$^{-1}$ (G band). A large amount of defects are presented in SL-BGQDs, giving rise to the Raman spectrum peak at 1345 cm$^{-1}$ (D band); here, the D band is activated by the destruction of the sp$^2$ hybridized graphene network due to sp$^3$ hybridized C atoms bonded to boron. The intensity ratio of the G to D bands was determined to be 1.1, indicating a high degree of graphitization because the signal of the ordered G band is similar to or slightly greater than the signal of the disordered D band.

Figure 12E:
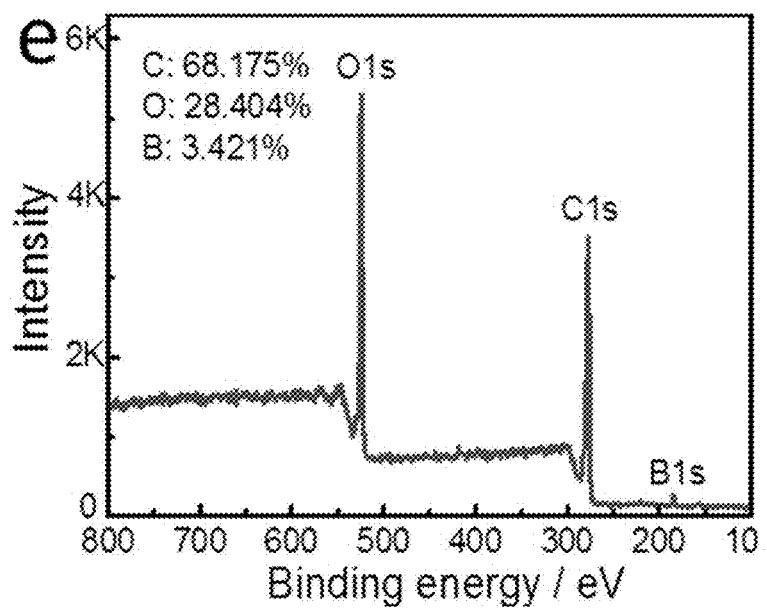

An analysis of the surface elemental characteristics of SL-BGQDs was carried out by X-ray photoelectron spectroscopy (XPS). The XPS survey shows that carbon (68.175%), oxygen (28.404%), and boron (3.421%) are present on the surface of SL-BGQDs (FIG. 12E). XPS analysis does not show the presence of any metal impurities, confirming the metal-free nature of SL-BGQDs. In the expanded high-resolution XPS spectra, the C 1s peaks at 284.7, 286.2, and 288.6 eV are assigned to carbon atoms in the form of C—C (sp$^3$)/C═C (sp$^2$), C—O (sp$^3$), and O—C═O (sp$^2$), respectively. The O 1s peaks at 532.1, 532.5, and 532.8 eV are associated with C═O quinone-type groups, C—OH phenol groups, and C—O—C ether groups, respectively. The B 1s peaks at 191.2 and 191.6 eV are attributed to sp$^2$ C═B bonds. In addition, the B 1s peak at 192.4 eV is associated with B—O bonds. The peaks at 191.2 and 191.6 eV further provide the evidence of the boron doping in SL-BGQDs.

Figure 12F:
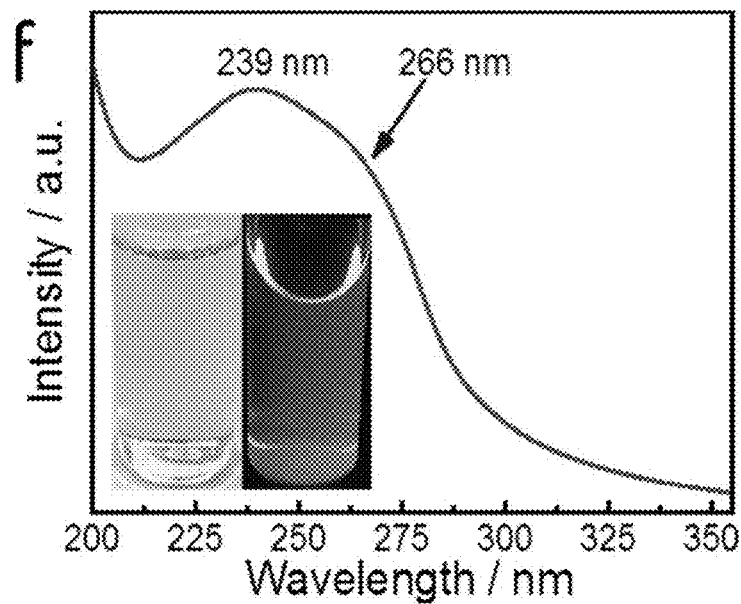

The UV absorption spectrum (FIG. 12F) of SL-BGQDs shows an absorption peak at about 239 nm resulting from π-π* transition of aromatic domains in SL-BGQDs. A shoulder peak at 266 nm is also observed, attributable to n-π* transition of carbonyl groups (C═O bonds) and the characteristic absorption peak of GQDs, which confirms the presence of functional groups. When aqueous dispersions of SL-BGQDs were exposed to UV light (365 nm), blue light was emitted from the dispersions (inset in FIG. 12F). The excitation wavelength-tunable, upconverted fluorescence from SL-BGQDs confirms their quantum confinement effect. Fourier transform infrared (FT-IR) spectrum analysis was used to evaluate additional surface properties of SL-BGQDs. The FT-IR absorption peaks at 3416 cm$^{-1}$ and 1714 cm$^{-1}$ were observed, corresponding to —OH and C═O stretching modes, respectively; these peaks signify the presence of hydroxyl and carboxyl groups on SL-BGQDs, which endows them with good water-solubility.

Figures 13A, 13B, 13C, 13D:
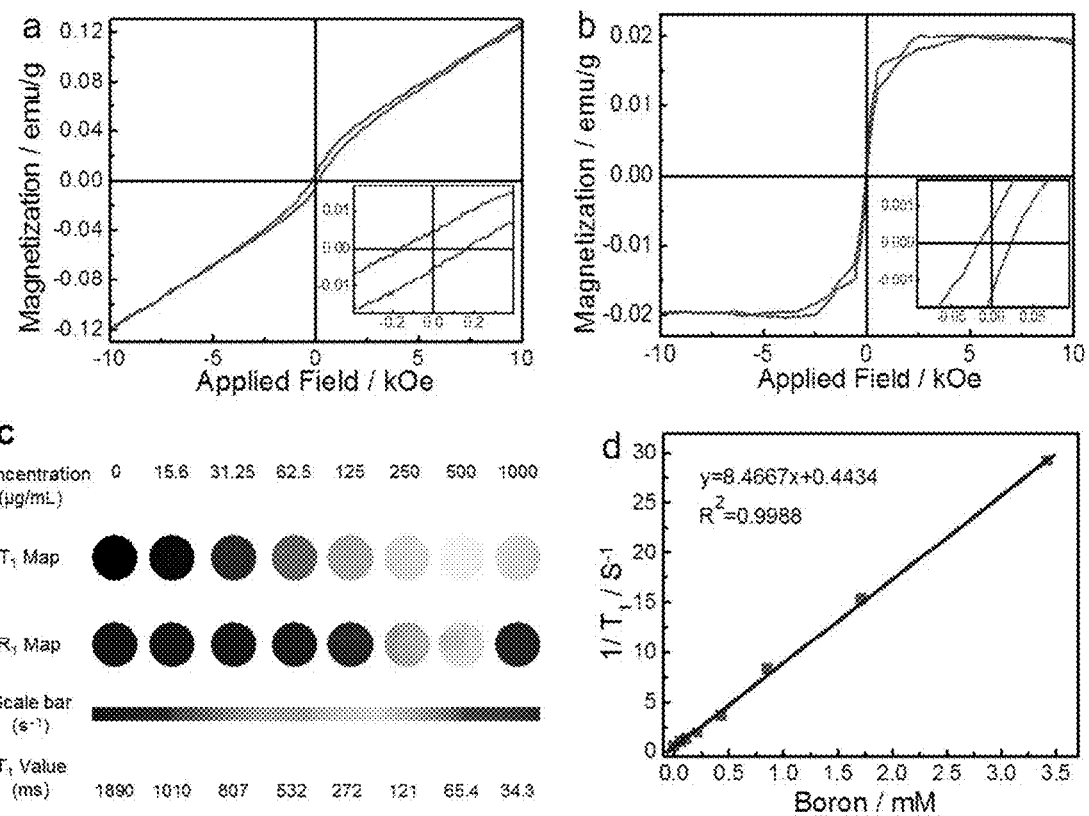
FIGS. 13A-13D illustrate magnetic properties and in vitro MRI of representative SL-BGQDs of the invention.

Magnetic properties of SL-BGQDs were assessed with a superconducting quantum interference device magnetometer (SQUID). FIG. 13A shows the magnetization hysteresis loop measured at a temperature of 6 K in the field range of −10 kOe<H<+10 kOe for SL-BGQDs, from which the saturation of magnetization is identified at about Ms=0.121 emu g$^{-1}$ after subtracting the diamagnetic background. The saturation of magnetization at 300 K for SL-BGQDs was similarly identified to be Ms=0.0197 emu g$^{-1}$ (FIG. 13B), which also indicates that SL-BGQDs have a very weak ferromagnetic ordering at room temperature. The magnetic properties of SL-BGQDs result from the break of π-bonds in boron-doped GQDs due to the missing C atoms, which induces unpaired electrons and partial spin polarization in SL-BGQDs. Importantly, the boron atoms in SL-BGQDs provide paramagnetic centers for $T_1$-weighted MR imaging since localized doping produces local magnetic moments and spins of dangling bonds (B—C bond).

To evaluate the applicability of using SL-BGQDs as contrast agents for MR imaging, quantitative $T_1$ and $T_1$-weighted MR imaging scan sequences were acquired of SL-BGQD samples in PBS at magnetic field strength of 14T. As shown in FIG. 13C, the $T_1$-weighted signal intensity increases with increasing SL-BGQD concentration (i.e., an increase in boron concentration). $1/T_1$ was then plotted against the boron molar concentration in SL-BGQDs (FIG. 13D). The relaxation rate $R_1$ (=$1/T_1$) exhibits a linear relationship with boron molar concentration, and the longitudinal relaxivity, n (the slope of the best fit line in this linear relation) of SL-BGQDs was evaluated to be 8.5 mM$^{-1}$ s$^{-1}$ (FIG. 13D). A concentration-dependent negative signal enhancement effect was clearly observed, and the $r_2$ value of SL-BGQDs was determined to be 9.2 mM$^{-1}$ s$^{-1}$ based on the linear relation between the transverse relaxation and boron molar concentrations.

There are two design principles that regulate the development of $T_1$ contrast agents: (i) n should be large ($r_1$>5) and (ii) the ratio of $r_2$ over n should be small (usually less than 5). Throughout the development of SL-BGQDs as $T_1$ contrast agents described herein, the relaxivity values and qualitative in vitro MR imaging results were compared to the gold standard clinical $T_1$ contrast agent: Gd-DTPA. As shown in, the n and $r_2$ relaxivity values of Gd-DTPA were determined to be 4.3 mM$^{-1}$ s$^{-1}$ and 5.03 mM$^{-1}$ s$^{-1}$, respectively, which yields $r_2/r_1$=1.17. The n value of the SL-BGQDs (FIG. 13D) was about two times greater than the longitudinal relaxivity of Gd-DTPA at 14 T, and the $r_2/r_1$ ratio for the SL-BGQDs was 1.08, similar to that of Gd-DTPA (1.17). With high $r_1$ and low $r_2/r_1$ ratio of SL-BGQDs have advantageous $T_1$ as contrast agents for $T_1$-weighted MR imaging.

Figures 14A, 14B, 14C:
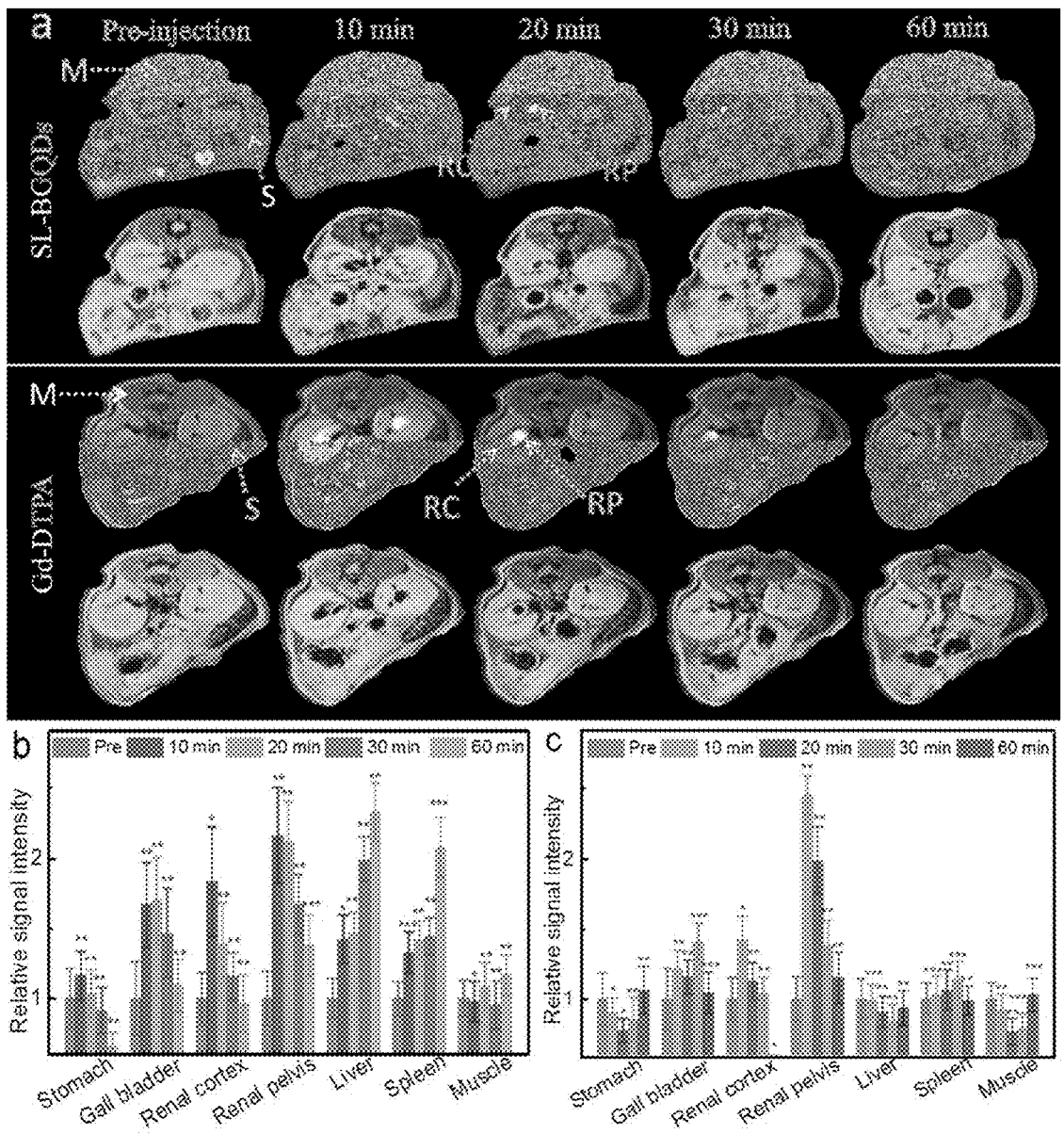
FIGS. 14A-14C compare in vivo abdominal MR imaging of mice treated with SL SL-BGQDs and Gd-DTPA intravascularly.
Figure 15:
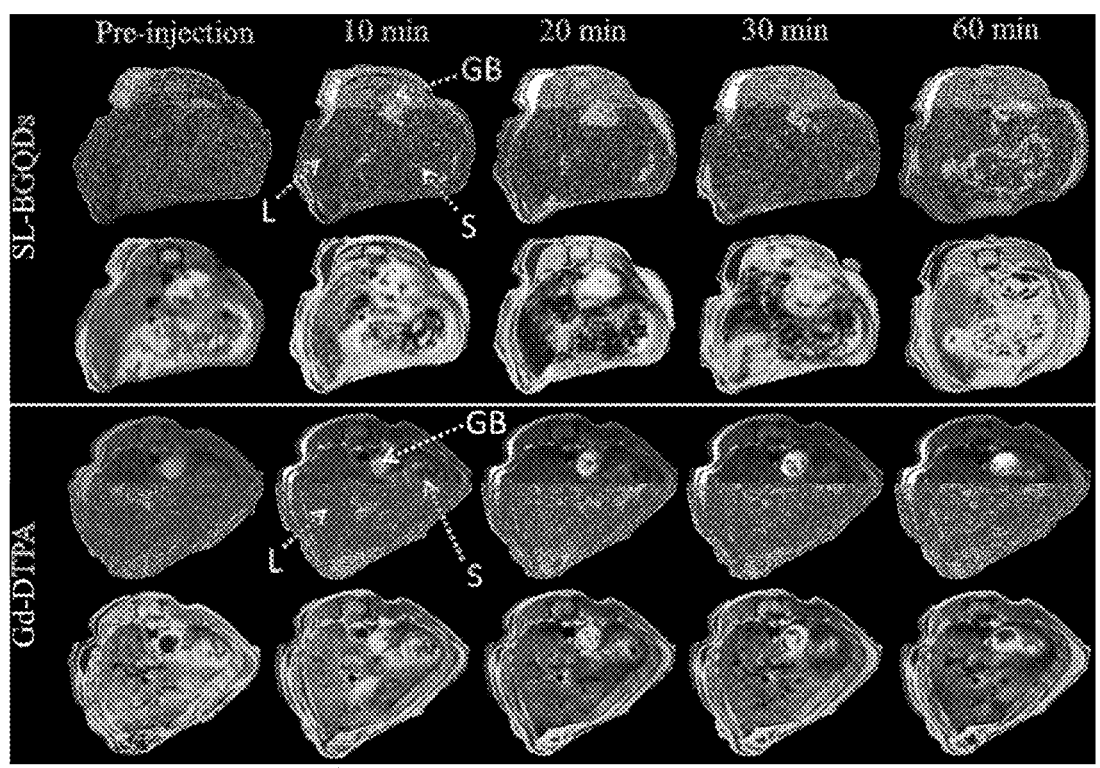
FIG. 15 compares in vivo abdominal MR imaging of mice treated with SL-BGQDs and Gd-DTPA: $T_1$-weighted MR images of the cross-sections of mice receiving SL-GQDs (top panel) and Gd-DTPA (bottom panel) treatments with dynamic time-resolved MR imaging acquired before and at various time points after intravenous contrast agent administration. Both grayscale and colorized images are displayed for each experimental group. The arrows denote various organs: liver (L), stomach (S), and gall bladder (GB).

An in vivo MR imaging assessment of SL-BGQDs was conducted with a 14 T MR imaging system using a C57BL/6 wild-type mouse model. 200 μL of SL-BGQDs (1 mg mL$^{-1}$) dispersed in PBS solution was administered via intravenous injection. As a comparison, the images were also acquired from mice similarly treated with Gd-DTPA at its clinical dosage (200 μL, 1 mg mL$^{-1}$). $T_1$-weighted MR images of the cross-sectional views of mice centered within the abdomen were acquired before and after contrast agent injection. As shown in FIG. 14A (showing the posterior abdomen) and FIG. 15 (showing the anterior abdomen), both SL-BGQDs and Gd-DTPA demonstrated a substantial signal enhancement in renal cortex (RC), renal pelvis (RP), and gall bladder (GB) as evidenced by comparing their pre-injection and post-injection images. In addition, SL-BGQDs demonstrated slightly better signal enhancement in liver and spleen than Gd-DTPA. For Gd-DTPA, the contrast enhancement peaked within the first 10 min post-injection, but rapidly declined between the 20 and 30 min imaging time points, was completely nullified by 60 min post-injection. SL-BGQDs demonstrated greater $T_1$-weighted contrast enhancement (brighter post-injection regions of interest) as well as a prolonged hyperintensive $T_1$-weighted signal in most of the organs analyzed (kidneys, liver, and spleen). These trends are further demonstrated by quantification of signal strengths (FIGS. 14B and 14C). The change in $T_1$-weighted signal between pre- and post-injection images in the liver and spleen of mice treated with SL-BQGDs at 60 min post-injection increased by 232.8% and 207.6%, respectively. In contrast, no $T_1$-weighted signal increase was detected in any organ in mice injected with Gd-DTPA at 60 min post-injection as compared to those acquired pre-injection.

Figure 16:
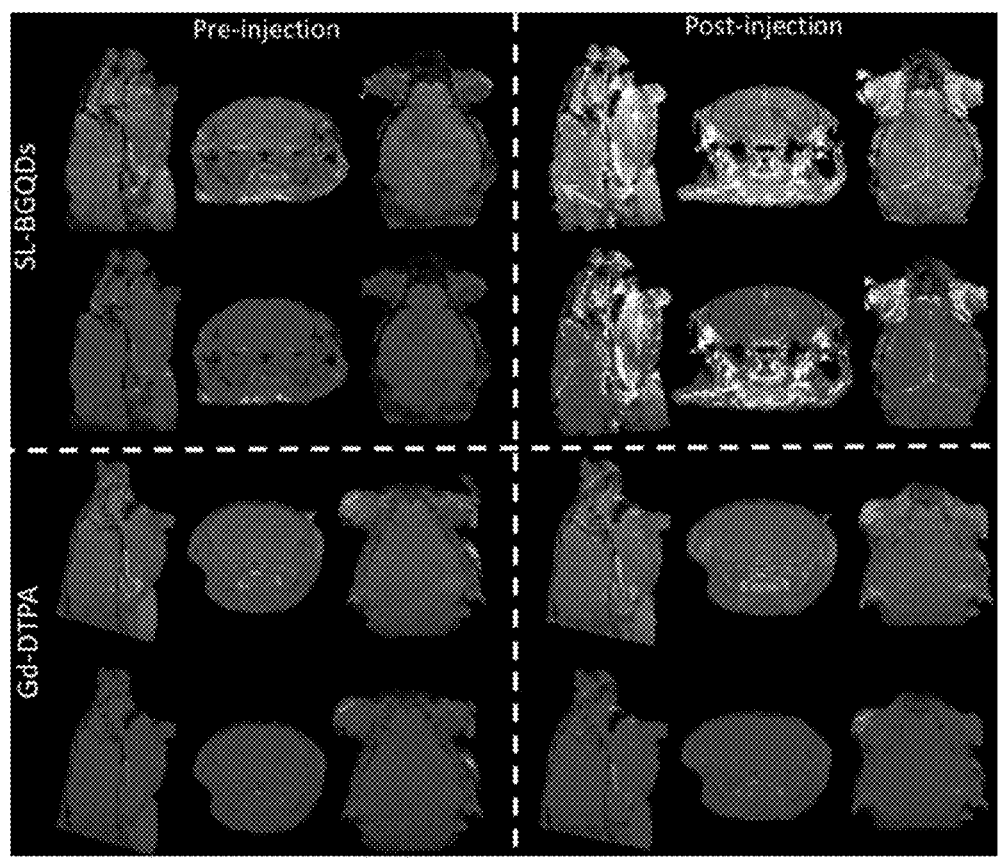
FIG. 16 compares in vivo cranial MR imaging: $T_1$-weighted MR images of the cross-sections of mice receiving SL-BGQD (upper panels) and Gd-DTPA (lower panels) treatments prior to (left panels) and 10 min after (right panels) intravenous injection of contrast agent. The yellow arrow notes the great cerebral vein and the red arrow notes the superior sagittal sinus.
Figures 17A, 17B, 17C, 17D, 17E, 17F, 17G, 17H:
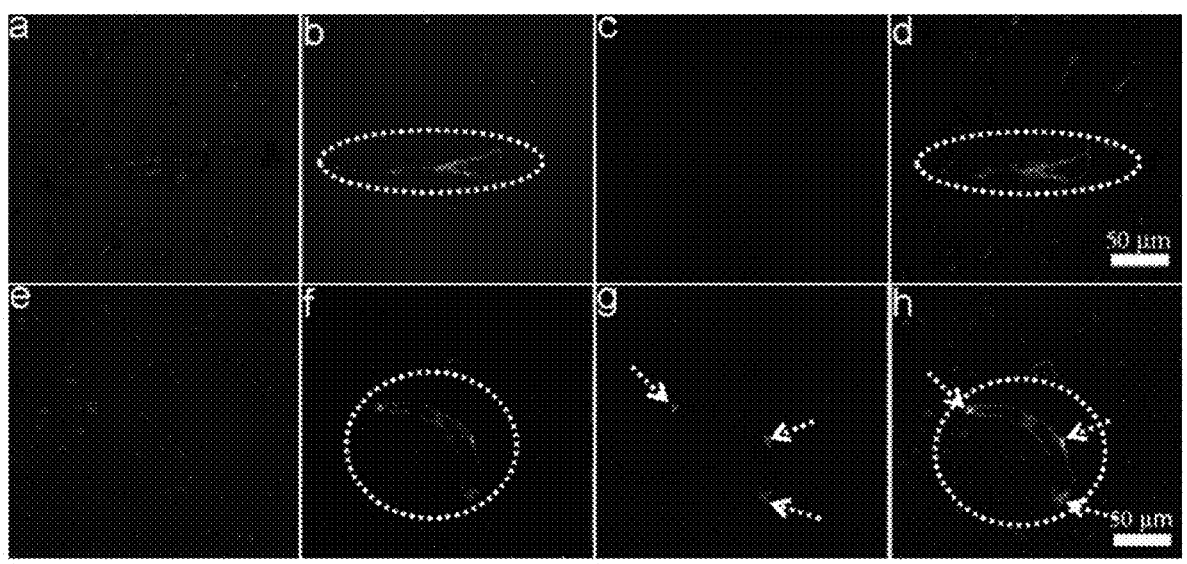
FIGS. 17A-17H compare confocal fluorescence microscopic images of mouse brain tissue sections acquired 1 h after mice received PBS injection (17A-17D) and SL-BGQDs (17E-17H). Cell nuclei were stained with DAPI (blue) (17A and 17E); endothelial cells were stained with anti-CD31 antibody (green) (5B and 5F); PBS was not present (red fluorescence, if any) (17C and 17G) and SL-BGQDs fluoresced red (indicated with white arrows) when they are excited with a 650 nm laser; overlaid images of mouse brain tissue (17D and 17H) from 17A-17C and 17E-17G, respectively. Blood vessels are encircled with white dashed circles.

To further evaluate the efficacy of SL-BGQDs as an in vivo $T_1$ contrast agent, performed cranial MR imaging was conducted to acquire a map of the neurovasculature of a mouse. Images of the entire head were acquired by a $T_1$-weighted MR scan sequence prior to and 10 min after injection of 200 μL, 5 mg mL$^{-1}$ of either SL-BGQDs or Gd-DTPA. FIG. 16 shows the maximum intensity projections of selected pre- and post-injection images for SL-BGQD (top panels) and Gd-DTPA (bottom panels) treated mice. Cranial blood vessels could hardly be identified in pre-injection images for either group. Conversely, the vasculature structures were clearly seen after SL-BGQD administration; the great cerebral vein was seen in the post-injection sagittal view (yellow arrow) and the superior sagittal sinus was evident in the post-injection coronal view (red arrow). Mice receiving Gd-DTPA with a dose identical to that SL-BGQD showed no apparent change in contrast between pre- and post-injection images. The great positive contrast enhancement provided by SL-BGQDs is attributed to their high $r_1$ relaxivity.

To evaluate the BBB permeability of SL-BGQDs, a property that is essential for neurological imaging, mice of wild type were treated intravenously injected with SL-BGQDs. Brain sections of mice were histologically analyzed 1 h post-injection. Tissue sections were stained with anti-CD31 antibody for visualization of endothelial blood vessels and with DAPI for cell nuclei. The brain tissues from PBS-treated mice as control showed no fluorescence signal 1 h post injection (FIGS. 17A-17D). In contrast, brain tissues of mice intravenously injected with SL-BGQDs exhibited red fluorescence 1 h post-injection (FIG. 17E-17H), confirming that SL-BGQDs bypassed the BBB and accumulate in the brain tissues of live mice.

In summary, single-layer, metal-free, ferromagnetic boron-doped graphene quantum dots (4.7 nm) are provided for MR $T_1$ weighted imaging contrast agent. The as-synthesized SL-BGQDs demonstrate high longitudinal relaxivity ($r_1$=8.5 mM$^{-1}$ s$^{-1}$) and a low $r_2/r_1$ ratio (1.08), and therefore may serve to enhance contrast in $T_1$-weighted MR imaging. These findings revealed that, at clinical doses for MR imaging applications, SL-BGQDs exhibit a more stable safety profile than a clinically used Gd-based $T_1$ contrast agent. In addition, SL-BGQDs can pass BBB and have much prolonged imaging time (about 60 min) as compared to Gd-DTPA (about 10 min). This well-characterized metal-free SL-BGQD contrast agent may serve as an improved version of Gd-based contrast agent for $T_1$-weight MR imaging in clinical applications than Gd-based $T_1$ contrast agents to improve the health, safety, and clinical benefits of cancer diagnosis and treatment.

As used herein, the term "about" refers to ±5 percent of the recited value.

The following examples are provided for the purpose of illustrating, not limiting, the invention.

Example 1

Preparation, Characterization, Properties, and Magnetic Resonance Imaging Using Representative Multilayer Boron-Doped Graphene Quantum Dots In this example, the preparation, characterization, and properties of representative multilayer boron-doped graphene quantum dots and their use in magnetic resonance imaging are described.

Synthesis of Multilayer Boron-Doped Graphene Quantum Dots (B-GQDs).

All chemicals were purchased from Aldrich. 4-Vinylphenylboronic acid (VPBA) (0.05 g) and boric acid (0.10 g) were dissolved in a solution of 30 mL acetone and 5 mL ethanol. After intense sonication for 30 min, 5.0 mL of $H_2O_2$ (30%) was slowly added into the solution. The solution was then treated ultrasonically for 10 min and transferred into a 50 mL Teflon-lined stainless autoclave. The precursor solution was heated to and maintained at 205° C. After 24 h, the solution was cooled naturally to room temperature. The resultant product was purified with repeated centrifugation at a speed of 20000 rpm for 20 min and redispersion in water for three cycles. Finally, the aqueous dispersion of B-GQDs was dialyzed for 3 days (Spectra/Per molecular porous membrane tubing, cutoff 12,000-14,000) at room temperature. The aqueous dispersion of B-GQDs was then collected and dried to obtain solid B-GQDs.

Synthesis of Graphene Quantum Dots (GQDs).

Phenol (0.05 g) was dissolved in a solution of 30 mL acetone and 5 mL ethanol. After sonication for 30 min, 5.0 mL of $H_2O_2$ (30%) was slowly added into the solution. The solution was then treated ultrasonically for 10 min and transferred into a 50 mL Teflon-lined stainless autoclave. The precursor solution was heated to and maintained at 205° C. After 24 h, the solution was cooled naturally to room temperature. The resultant product was purified with repeated centrifugation at a speed of 20000 rpm for 20 min and redispersion in water for three cycles. Finally, the aqueous dispersion of GQDs was dialyzed for 3 days (Spectra/Por molecular porous membrane tubing, cutoff 12,000-14,000) at room temperature. The aqueous dispersion of GQDs was then collected and dried to obtain solid GQDs.

Cell Culture.

Human glioblastoma cells (SF-763), breast cancer cells (BT-474), and human embryonic kidney cells (HEK293T) were purchased from the American Type Culture Collection (Manassas, Va., ATCC) and grown in Dulbecco's Modified Eagle's Medium (DMEM) supplemented with 10% fetal bovine serum and 1% antibiotic-antimycotic (Life technologies, Grand Island, N.Y.). Cells were cultured in an incubator maintained at 37° C., 5% $CO_2$ and 95% humidity.

Confocal Laser Scanning Microscopic Imaging.

SF-763 cells were seeded onto glass cover slips in a 6-well plate. After overnight incubation in water at 37° C., cells were incubated with B-GQDs (5 µg/mL) for 2 h. Cells were then washed with PBS 3× and fixed with 4% paraformaldehyde for 10 min at 37° C. Cells were then mounted onto glass slides with ProLong® Gold Antifade Mountant (Life Technologies Inc., Gaithersburg, Md.). The images of cells were acquired using a Laser Scanning Microscope Leica SP8X (Leica Microsystems GmbH, Germany). Three excitation wavelengths were used (405, 488, and 546 nm).

Two-photon fluorescent imaging. SF-763 cells were seeded onto glass cover slips in a 24-well plate. Twenty four hours after seeding, cells were incubated with B-GQDs (5 µg/mL) for 2 h. Cells were then washed with PBS 3× and fixed with 4% paraformaldehyde for 10 min at 37° C. Cells were nuclear-stained with DAPI and then mounted onto glass slides with ProLong® Gold Antifade Mountant (Life Technologies Inc., Gaithersburg, Md.). Two-photon imaging was performed using an Olympus FV1000 MPE BX61 multi-photon microscope at an excitation wavelength of 900 nm.

In Vivo NIR Imaging of B-GQDs.

All animal studies were conducted in accordance with University of Washington's Institute of Animal Care and Use Committee (IACUC) approved protocols as well as with federal guidelines. B-GQDs (200 µL, 1 mg/mL) were injected subcutaneously or intravenously into athymic nude mice (Jackson Labs, Bar Harbor, Me.). Fluorescence images as well as photographs were taken by a Xenogen IVIS imaging system (PerkinElmer Inc.).

Viability of Cells Treated with Representative B-GQDs.

Cells were seeded in a 96-well plate and incubated overnight in the aforementioned DMEM. In the following day, the medium was replaced with a medium containing B-GQDs or with medium control. Three concentrations of B-GQDs (50, 25 and 12.5 µg/mL) were used, and samples at each concentration were run in sextuplicate. The cells were incubated with B-GQDs for 72 h. Cells in wells containing the medium without B-GQDs were used as the control. Cell viability was assessed using the Alamar Blue assay. Briefly, the medium was replaced with cell culture medium containing the Alamar Blue reagent and incubated for 2 h. Following the incubation, a microplate reader (SpectraMax i3, Molecular Devices, Sunnyvale, Calif.) was used to determine the fluorescence intensity of B-GQDs (550 ex/590 em). The fluorescence intensity from B-GQDs in treated cells was compared to the intensity from untreated control cells to determine percent viability.

Histopathological Evaluation.

Five days after receiving intravenous administration of B-GQDs at 1 mg/mL, the C57BL/6 wild-type mice (Charles River Laboratories, Inc.) were euthanized and the whole organs (heart, kidney, liver, lung and spleen) were removed and preserved in 10% formalin for 48 h. Tissues were then embedded in paraffin, sliced into 5 µm sections, and stained with hematoxylin and eosin. Microscopic images of tissues were acquired using a Nikon ECLIPSE TE2000-S microscope.

Hematology Assay.

Blood cell panels including white blood cells and platelet and serum alanine aminotransferase and blood urea nitrogen levels were quantified at 24 h after intravenous administration of 200 µL of 1 mg/mL B-GQDs in C57BL6 wild-type mice (n=4). Animals receiving PBS injection (n=4) were used as controls. Blood was drawn from each mouse through cardiac puncture, and submitted to the Research Testing Services at University of Washington for analysis.

Biodistribution and Blood Circulation of Representative B-GQDs.

C57BL6 wild-type mice were injected via tail vein with 200 µL of 1 mg/mL of B-GQDs. Mice receiving no injection were used as controls. At 2 h, 24 h, 48 h and 72 h after injection, the mice were euthanized and the whole organs of liver, spleen, kidney, lung, and heart were harvested. Fluorescence was acquired for each tissue type using a Xenogen IVIS imaging system at an excitation wavelength of 710 nm.

For assessment of serum half-life, blood was collected from mice at 0.15, 1, 1.5, 2, 2.5, 3, 4, 6, 8, and 10 h after injection of 200 µL of 1 mg/mL of B-GQDs. Blood was centrifuged, and plasma was collected. Plasma from mice receiving no B-GQD injection was used to eliminate the background fluorescence. Fluorescence was acquired using a Xenogen IVIS imaging system at an excitation wavelength of 710 nm.

In Vitro MRI.

$T_1$-weighted imaging and quantitative $T_1$ MRI scan sequences were used to investigate the contrast enhancing capabilities of B-GQDs and GQDs. MRI was conducted on a Bruker Avance III 600 MHz, 14 T wide bore spectrometer. B-GQDs or GQDs in phosphate buffered saline were pipetted into glass vials (3.25 mm I.D., 5 mm O.D., 200 µL volume). The vials were fixed in place inside a water reservoir; the water served as a homogeneous background signal to minimize magnetic susceptibility variations near samples. The secured vials were placed in a 25 mm single-channel $^1$H radiofrequency receiving coil (PB Micro 2.5). Relaxation properties of B-GQDs and GODs were quantitatively evaluated with a quantitative $T_1$ rapid imaging with refocused echoes and variable repetition time (RARE-VTR) pulse sequence with echo time (TE) of 12.0 ms, TR=80 ms, 400 ms, 800 ms, 1600 ms, 3000 ms, 6000 ms, 8000 ms, and 12000 ms, 180×180 µm² in-plane resolution and 5.0 mm slice thickness for one slice. $T_1$-weighted images were acquired with a RARE pulse sequence with TE=5.49 ms, TR=531 ms, 78×52 µm² in-plane resolution and 0.5 mm slice thickness for 10 slices. Analysis of MRI data was accomplished with the FMRIB software library (FSL), Paravision 5.1 analysis package (Bruker), and ImageJ (NIH). $T_1$ values were determined within a circular, 100-voxel region of interest.

In vivo MRI. 100 min interleaved $T_1$-weighted imaging was performed on C57BL/6 wild-type mice prior to and after B-GQDs (100 µL, 1 mg/mL) injection, using a Bruker Avance III 600 MHz, 14 T vertical-bore imaging system. Mice were anesthetized with isoflurane (Piramal Healthcare), and fixated in a coil-integrated respiratory monitoring system (SA Instruments; MR-compatible small animal monitoring and gating system) with nose-cone for oxygen/anesthetic, ear-bar head holder, circulating temperature control bath, respiratory monitoring, and residual gas extraction. Abdominal scans were acquired using rapid acquisition with refocused echoes (RARE) $T_1$-weighted (TR/TE=691/5.5 ms, in-plane resolution 93×62 µm², matrix 256×284) sequences with slices placed in the transverse plane with 0.5 mm slice thickness and 0.75 mm interslice gap allowing for coverage from the liver to the pelvic floor.

Characterization.

Atomic force microscopy (AFM) analyses were performed on a stand-alone AFM system (Bruker Dimension Icon-PT). TEM and high-resolution TEM images were acquired on a Tecnai G2 F20 electron microscope (FEI, Hillsboro, Oreg.) operating at a voltage of 200 kV. Powder X-ray diffraction (XRD) patterns were acquired from lyophilized samples using D8 Bruker X-ray diffractometer with Cu Kα radiation. UV-vis absorption spectra were obtained on a UV-vis Spectrometer (Agilent Technologies, Santa Clara, Calif.). Magnetic properties were evaluated using a superconducting quantum interference device magnetometer (Quantum Design MPMS XL-7). Fourier transform infrared (FTIR) spectra were acquired using a Nicolet 5-DXB FTIR spectrometer with a resolution of 4 $cm^{-1}$. Raman spectra were taken on a Raman-Microscope (Renishaw-InVia) using an $Ar^+$ laser with 514.5 nm at room temperature. PL spectra were obtained on a JOBIN YVON Co. FluoroMax®3 Spectrofluorometer equipped with a Hamamatsu R928P photomultiplier tube. X-ray photoelectron spectroscopy (XPS) experiments were conducted at the National ESCA and Surface Analysis Center at University of Washington. Inductively coupled plasma atomic emission spectroscopy (ICP-AES, Perkin Elmer Optima 8300) was used to further test if the metal atoms are present in carbon samples.

Example 2

Preparation, Characterization, Properties, and Magnetic Resonance Imaging Using Representative Single Layer Boron-Doped Graphene Quantum Dots In this example, the preparation, characterization, and properties of representative single layer boron-doped graphene quantum dots and their use in magnetic resonance imaging are described.

Synthesis of Single-Layer Boron-Doped Graphene Quantum Dots (SL-BGQDs).

All chemicals were purchased from Sigma-Aldrich (St. Louis, Mo., USA). VPBA (0.05 g) and boric acid (0.03 g) were dissolved in a solution of 20 mL acetone and 5 mL ethanol. After intense sonication for 30 min, 10.0 mL of $H_2O_2$ (30%) was slowly added to the solution. The solution was then ultrasonicated for 10 min and transferred into a 50 mL Teflon-lined, stainless-steel autoclave. This precursor solution was heated to and maintained at 205° C. After 24 h, the solution was cooled naturally to room temperature. The resultant solution was dialyzed (Spectra/Per molecular porous membrane tubing, cutoff 14 kDa) for 3 days at room temperature. The aqueous dispersion of SL-BGQDs was then collected and centrifuged at 14,800 rpm for 30 min and the supernatant was discarded.

Characterization.

Transmission electron microscopy (TEM) and high-resolution TEM (HRTEM) images were acquired on a Tecnai G2 F20 electron microscope (FEI, Hillsboro, Oreg.) operating at a voltage of 200 kV. Atomic force microscopy (AFM) was performed using a Veeco DI Nano-scope MultiMode V system. Powder X-ray diffraction (XRD) patterns were acquired from lyophilized samples using a D8 Bruker X-ray diffractometer with Cu Kα radiation. UV-vis absorption spectra were obtained on a UV-vis Spectrometer (Agilent Technologies, Santa Clara, Calif.). Magnetic properties were measured using a superconducting quantum interference device magnetometer (Quantum Design MPMS XL-7). Fourier transform infrared (FTIR) spectra were acquired using a Nicolet 5-DXB FTIR spectrometer with a resolution of 4 $cm^{-1}$. Raman spectra were acquired on a Raman-Microscope (Renishaw-InVia) using a 514.5 nm $Ar^+$ laser at room temperature. Photoluminescent (PL) spectra were obtained on a JOBIN YVON Co. FluoroMax®-3 Spectrofluorometer equipped with a Hamamatsu R928P photomultiplier tube. X-ray photoelectron spectroscopy (XPS) experiments were conducted at the National ESCA and Surface Analysis Center at the University of Washington.

Penetration of the Blood-Brain Barrier by SL-BGQDs.

All procedures involving animal studies were performed in accordance with University of Washington Institutional Animal Care and Use Committee regulations. C57BL/6 wild-type mice (Charles River Laboratories, Inc.) were euthanized 1 h post tail-vein injection with SL-BGQDs (dispersed in PBS, 200 μL, 1 mg $mL^{-1}$) or PBS (200 μL, control), and brain tissues were dissected. Tissues were preserved in 10% formalin for 48 h. Formalin-fixed tissue samples were first transferred from PBS to and maintained for 2 h in 70% ethanol and were then transferred into and maintained for an additional 2 h in 95% ethanol/5% methanol. Next, the samples were transferred to and maintained for 1 h in absolute ethanol and then transferred again into and maintained in 3 consecutive absolute xylene solutions, each for 1 h. After a dehydration step, the samples were placed in 2 consecutive melted paraffin baths, each for 2 h. The paraffin-penetrated samples were then embedded in paraffin blocks, sectioned at 10 μm thickness and loaded onto microscope slides. The loaded slides were first heated to remove excess paraffin and adhere the samples to the slides. Subsequently, the samples were deparaffinized by a series of xylene, ethanol, and PBS baths. Slides were then rinsed and stained with DAPI and anti-CD31 antibody for 15 min at room temperature. Coverslips were then mounted onto microscope slides using Prolong Gold Antifade Mountant. Images were acquired on a Leica SP8X confocal laser scanning microscope.

In Vitro MR Imaging.

$T_1$- and $T_2$-weighted imaging and quantitative $T_1$ and $T_2$ MR imaging scan sequences were used to investigate the contrast enhancing capabilities of SL-BGQDs. MR imaging was conducted on a Bruker Avance III 600 MHz, 14 T wide bore spectrometer. Either SL-BGQDs or Gd-DTPA samples in PBS were pipetted into glass vials (3.25 mm I.D., 5 mm O.D., 200 μL volume). The vials were fixed in place inside a water reservoir; the water served as a homogeneous background signal to minimize magnetic susceptibility variations near samples. The secured vials were placed in a 25 mm single-channel $^1H$ radiofrequency receiving coil (PB Micro 2.5). Relaxation properties of SL-BGQDs and Gd-DTPA were evaluated with a quantitative $T_1$ rapid imaging with refocused echoes and variable repetition time (RARE-VTR) pulse sequence with an echo time (TE) of 12.0 ms, TR=80 ms, 400 ms, 800 ms, 1600 ms, 3000 ms, 6000 ms, 8000 ms, and 12000 ms, 180×180 $\mu m^2$ in-plane resolution, and 5.0 mm slice thickness for one slice. Quantitative $T_2$ values were measured using a multi-spin multi-echo (MSME) pulse sequence with TR=2500 ms, TE=6.7+6n ms (n=0-16), and 78×156 $\mu m^2$ in-plane resolution with 0.5 mm slice thickness for 14 slices. $T_1$-weighted images were acquired with a RARE pulse sequence with TE=5.49 ms, TR=531 ms, 78×52 $\mu m^2$ in-plane resolution and 0.5 mm slice thickness for 10 slices. $T_2$-weighted images were acquired with a RARE pulse sequence with TE=6.78 ms, TR=4000 ms, and 78×52 $\mu m^2$ in-plane resolution with 0.5 mm slice thickness for 14 slices. Analysis of MR imaging data was accomplished with the FMRIB software library (FSL), Paravision 5.1 analysis package (Bruker), and ImageJ (NIH). $T_1$ values were determined within a circular, 100-voxel region of interest.

In Vivo MRI.

90 min sequential $T_1$-weighted imaging was performed over the abdominal regions of C57BL/6 wild-type mice prior to and after the injection of SL-BGQDs (200 µL, 1 mg mL$^{-1}$) or Gd-DTPA (200 µL, 1 mg mL$^{-1}$), using a Bruker Avance III 600 MHz, 14 T vertical-bore imaging system. Similarly, 10 min sequential $T_1$-weighted imaging was performed over the cranial regions of C57BL/6 wild-type mice prior to and after the injection of SL-BGQDs (200 µL, 5 mg mL$^{-1}$) or Gd-DTPA (200 µL, 5 mg mL$^{-1}$). Mice were anesthetized with isoflurane (Piramal Healthcare) and secured in a coil-integrated respiratory monitoring system (SA Instruments; MR-compatible small animal monitoring and gating system) with nose-cone for oxygen/anesthetic, ear-bar head holder, circulating temperature control bath, and residual gas extraction. Abdominal scans were acquired using rapid acquisition with refocused echoes (RARE) $T_1$-weighted (TR/TE=691/5.5 ms, in-plane resolution 93×62 µm$^2$, matrix 256×284) sequences and slices placed in the transverse plane with 0.5 mm slice thickness and 0.75 mm interslice gaps allowing for coverage from the liver to the pelvic floor. Cranial scans were acquired over the entire head with a 3-dimensional, $T_1$-weighted fast low angle shot (FLASH) scan sequence (TR/TE=16.2/2.7 ms, resolution 106×108×152 µm$^3$, matrix 284×186×132). Images from this cranial scan sequence were processed using a maximum intensity projection with a 3 mm slab thickness.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of obtaining a $T_1$-weighted magnetic resonance image of a tissue, comprising:
    (a) administering an effective dose of a contrast agent to a subject having a tissue to be imaged, wherein the contrast agent is a boron-doped graphene quantum dot; and
    (b) subjecting the subject to magnetic resonance imaging to provide a $T_1$-weighted magnetic resonance image of the subject's tissue.

2. The method of claim 1, wherein the tissue is heart, lung, liver, kidney, stomach, spleen, or brain tissue.

3. The method of claim 1, wherein the tissue is muscle tissue or vascular tissue.

4. The method of claim 1, wherein the contrast agent is administered intravenously or subcutaneously.

5. The method of claim 1, wherein the contrast agent is administered as a pharmaceutically acceptable composition.

6. The method of claim 1, wherein the effective amount of contrast agent is from about 5 to about 50 mg/kg subject.

7. The method of claim 1, wherein the boron-doped graphene quantum dot has a ratio of transverse relaxivity ($r_2$) to longitudinal relaxivity ($r_1$) from about 1 to about 5 at a magnetic field strength of from about 3 to about 14 T.

8. The method of claim 1, wherein the boron-doped graphene quantum dot comprises graphene having from one to four graphene layers.

9. The method of claim 1, wherein the boron-doped graphene quantum dot comprises from about 2 to about 8% boron atoms based on total number of carbon, oxygen, and boron atoms in the graphene quantum dot as measured by X-ray photoelectron spectroscopy (XPS).

10. The method of claim 1, wherein the boron-doped graphene quantum dot is substantially metal free.

* * * * *